(12) United States Patent
Sugiyama et al.

(10) Patent No.: US 8,708,892 B2
(45) Date of Patent: Apr. 29, 2014

(54) ENDOSCOPE WITH CONTROLLED BENDING SECTIONS

(71) Applicant: Olympus Medical Systems Corp., Tokyo (JP)

(72) Inventors: Yuta Sugiyama, Hino (JP); Hideki Tanaka, Tama (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/626,559

(22) Filed: Sep. 25, 2012

(65) Prior Publication Data

US 2013/0109919 A1  May 2, 2013

Related U.S. Application Data

(63) Continuation of application No. PCT/JP2012/054088, filed on Feb. 21, 2012.

(30) Foreign Application Priority Data

Mar. 29, 2011 (JP) ................................. 2011-073039

(51) Int. Cl.
  *A61B 1/00* (2006.01)
  *A61B 19/00* (2006.01)
  *A61B 1/005* (2006.01)
  *A61M 25/01* (2006.01)

(52) U.S. Cl.
  CPC ........... *A61B 19/5244* (2013.01); *A61B 1/0051* (2013.01); *A61M 25/0147* (2013.01)
  USPC ........ 600/117; 600/118; 600/146; 604/95.01; 604/95.04

(58) Field of Classification Search
  USPC .......................... 600/117, 118, 146, 148, 152; 604/95.01, 95.04, 95.05
  See application file for complete search history.

(56) References Cited

U.S. PATENT DOCUMENTS 5,876,325 A * 3/1999 Mizuno et al. ................. 600/118
6,468,203 B2 * 10/2002 Belson .......................... 600/146

(Continued)

FOREIGN PATENT DOCUMENTS

EP   1 892 009 A1   2/2008
EP   2 165 641 A2   3/2010

(Continued)

OTHER PUBLICATIONS

International Search Report issued in International Application No. PCT/JP2012/054088 on Mar. 27, 2012 (with translation).

(Continued)

*Primary Examiner* — Anhtuan T Nguyen
*Assistant Examiner* — Aaron B Fairchild
(74) *Attorney, Agent, or Firm* — Oliff PLC

(57) ABSTRACT

An endoscope including: two bending portions, a bending amount calculator, a setting portion, a determination portion, and a controller, configured as such: Upon bending of the distal bending portion, the bending amount calculator calculates the bending amount of the distal bending portion. If the determination portion finds if the bending calculated exceeds a first set threshold set by the setting portion, the controller continuously outputs a signal to drive the proximal bending portion to bend in the same direction as the distal bending portion. When subsequently the determination portion finds that the bending calculated is less than a second threshold less than the absolute value of the first threshold, and which is also set by the setting portion, the controller outputs a signal to return the proximal bending section to its initial predetermined position.

8 Claims, 14 Drawing Sheets

(56) References Cited

U.S. PATENT DOCUMENTS

| | | |
|---|---|---|
| 2002/0058858 A1 | 5/2002 | Ogura et al. |
| 2009/0287054 A1 | 11/2009 | Dejima et al. |
| 2010/0069719 A1 | 3/2010 | Wehrheim |

FOREIGN PATENT DOCUMENTS

| | | |
|---|---|---|
| JP | A-62-292134 | 12/1987 |
| JP | A-4-246322 | 9/1992 |
| JP | A-6-217919 | 8/1994 |
| JP | A-2004-230189 | 8/2004 |
| JP | A-2009-279405 | 12/2009 |
| JP | A-2010-201 | 1/2010 |
| JP | A-2010-220961 | 10/2010 |
| WO | WO 2011/040104 A1 | 4/2011 |

OTHER PUBLICATIONS

Extended European Search Report issued in European Patent Application No. 12763890.6 dated May 28, 2013.

Oct. 10, 2013 English Translation of the International Preliminary Report on Patentability issued in International Application No. PCT/JP2012/054088.

* cited by examiner

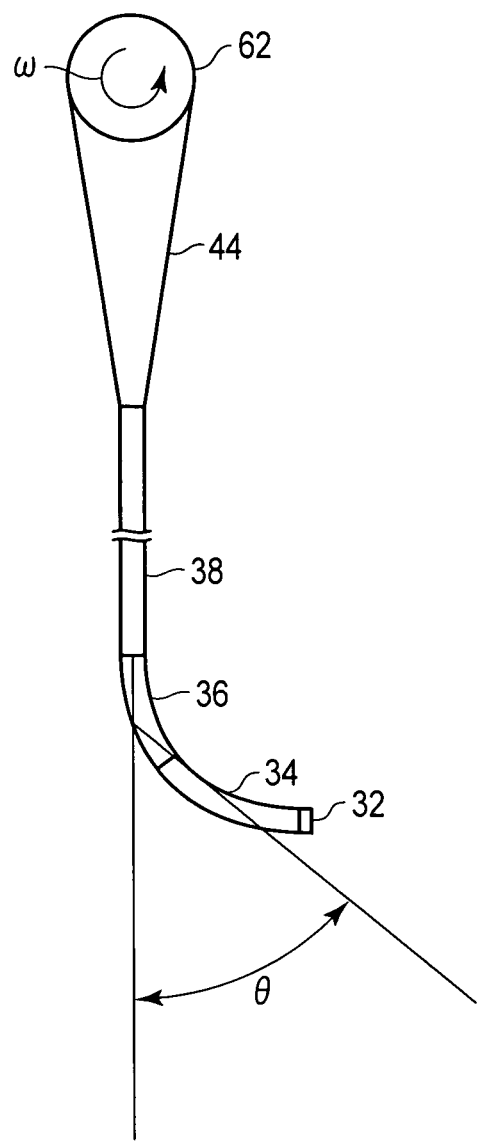
F I G. 3B

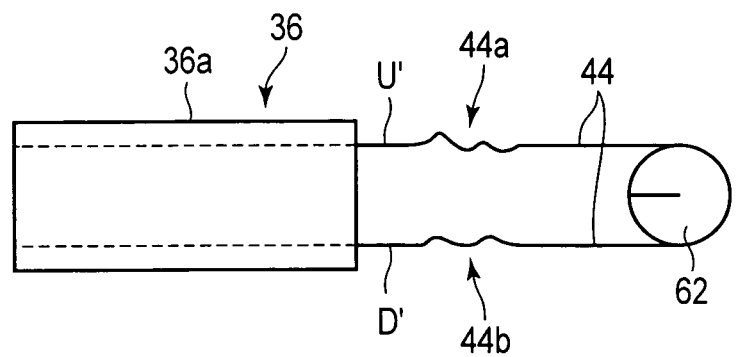
F I G. 4A
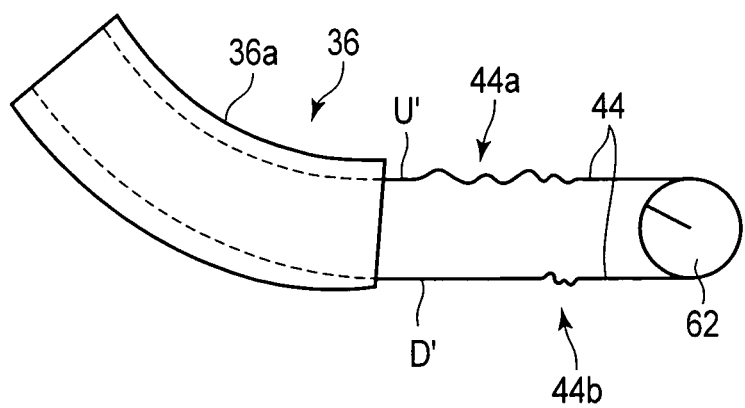
F I G. 4B

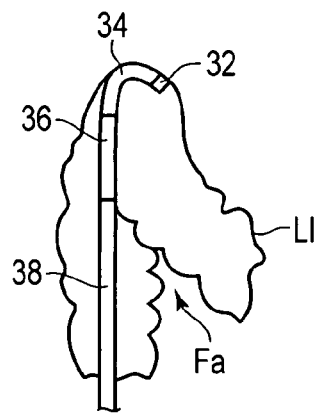
F I G. 7D
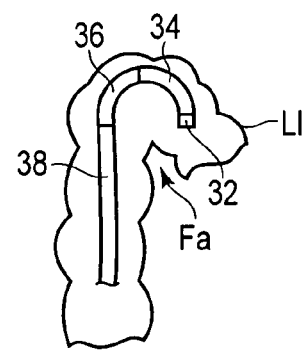
F I G. 7E
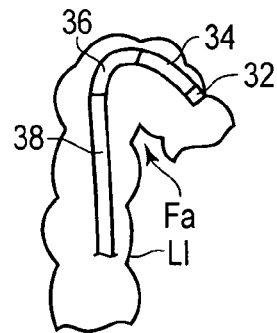
F I G. 7F

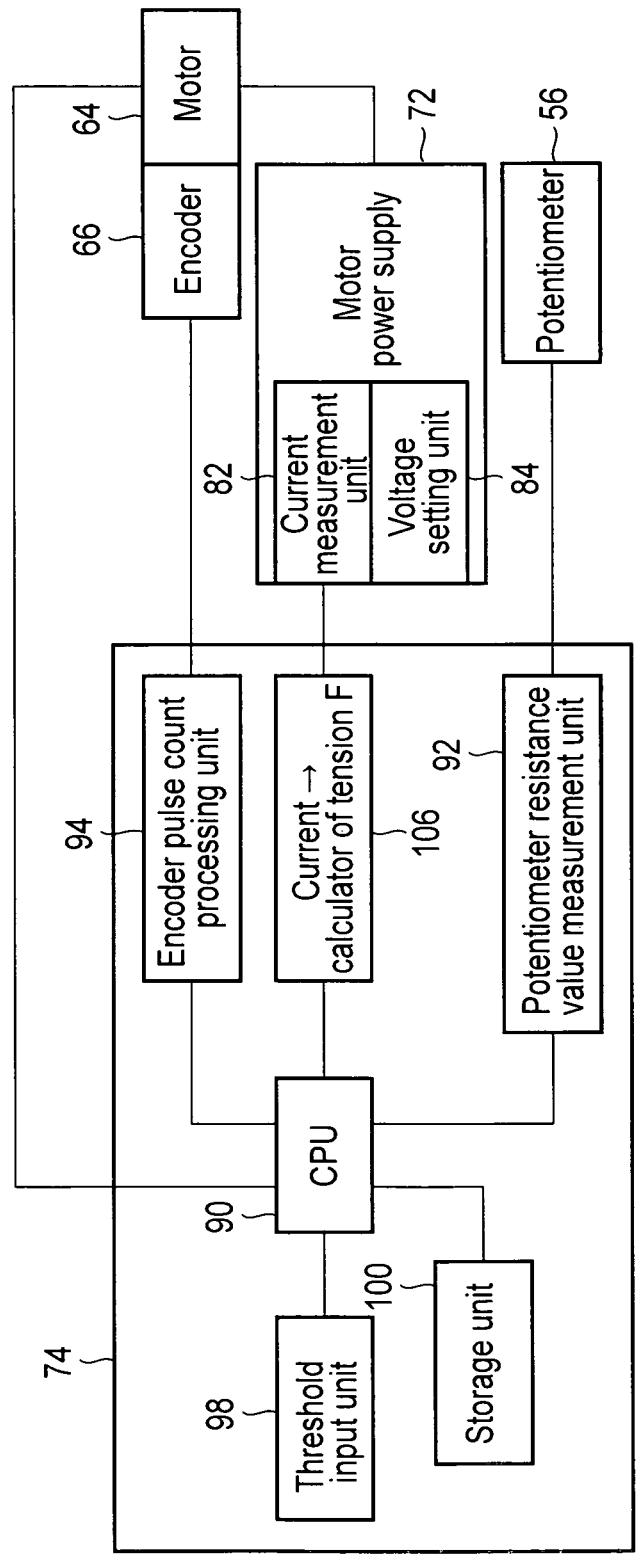
F I G. 10

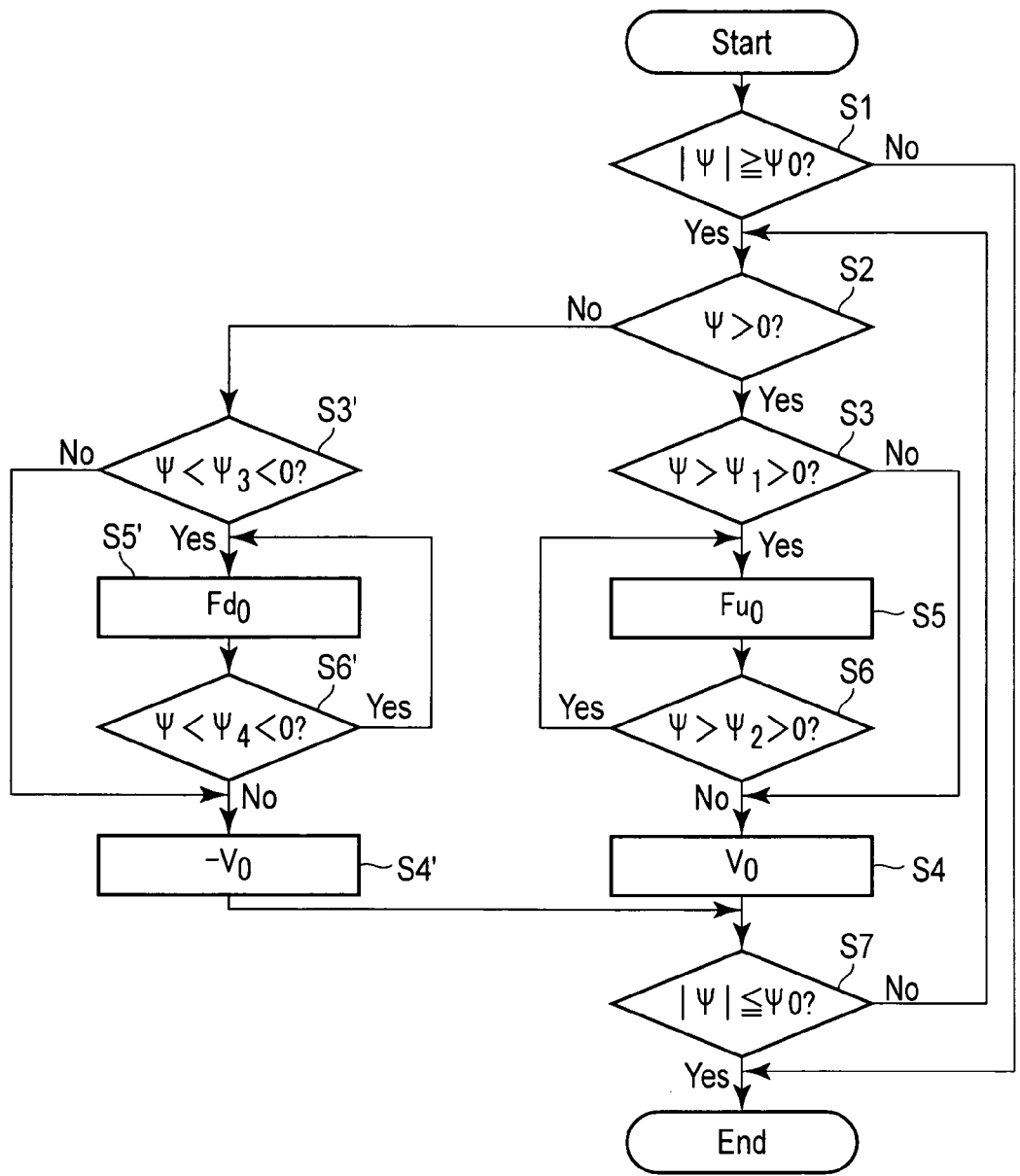
F I G. 11

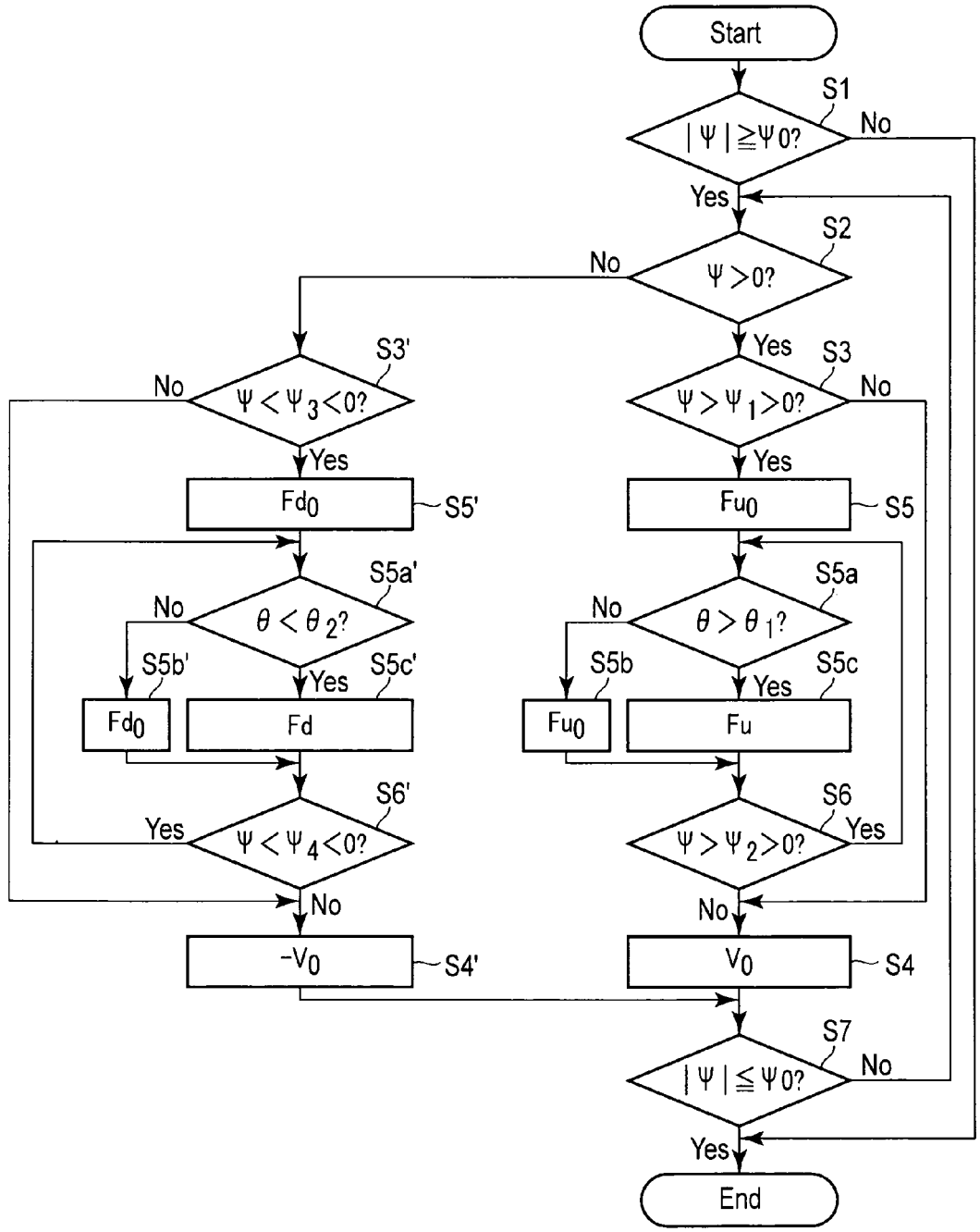
F I G. 12

ENDOSCOPE WITH CONTROLLED BENDING SECTIONS

CROSS-REFERENCE TO RELATED APPLICATIONS

This is a Continuation application of PCT Application No. PCT/JP2012/054088, filed Feb. 21, 2012, which was published under PCT Article 21(2) in Japanese.

This application is based upon and claims the benefit of priority from the prior Japanese Patent Application No. 2011-073039, filed Mar. 29, 2011, the entire contents of which are incorporated herein by reference.

BACKGROUND OF THE INVENTION

1. Field of the Invention

This invention relates to an endoscope having two bending portions.

2. Description of the Related Art

For example, Jpn. Pat. Appln. KOKAI Publication No. 6-217929 has disclosed an endoscope having first and second two bending portions. The endoscope allows a switch to be operated to store the shape of the first bending portion and manipulate the second bending portion so that the second bending portion will be in the same shape as the stored shape of the first bending portion.

BRIEF SUMMARY OF THE INVENTION

An endoscope according to the invention includes: an insertion portion which includes a first bending portion and a second bending portion provided on the proximal side of the first bending portion; an operation portion which is provided on the proximal side of the insertion portion, and which includes a first bending operation input portion configured to input a bending operation to bend the first bending portion; an input amount detector which is configured to detect, as a bending operation input amount, the bending operation input to the first bending operation input portion; a first bending drive mechanism which is configured to bend the first bending portion to a bending amount corresponding to the bending operation input amount; a bending amount calculator which is configured to calculate a bending amount of the first bending portion driven to bend by the first bending drive mechanism; a second bending drive mechanism which is configured to bend the second bending portion; a driving portion which is coupled to the second bending drive mechanism and which is configured to generate driving force to drive the second bending drive mechanism; a setting portion which is configured to set a first threshold stored in advance and compared with the bending amount of the first bending portion; a determination portion which is configured to determine whether the bending amount of the first bending portion calculated by the bending amount calculator is more than the first threshold; and a controller which is configured to continuously output, to the driving portion, a bending drive signal that drives the second bending drive mechanism to bend the second bending portion in the same direction as the bending direction of the first bending portion when the determination portion determines that the bending amount of the first bending portion is more than the first threshold.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3B is a schematic diagram showing a state in which the second bending portion is bent when the third drum of the operation portion of the endoscope is rotated in the endoscope system according to the first to third embodiments;

FIG. 4A is a schematic diagram showing a location between the second bending portion and the operation portion to bend the second bending portion of the insertion portion of the endoscope and showing the second bending portion in a straight state in the endoscope system according to the first and second embodiments;

FIG. 4B is a schematic diagram showing a location between the second bending portion and the operation portion to bend the second bending portion of the insertion portion of the endoscope and showing the second bending portion bent in a U-direction in the endoscope system according to the first and second embodiments;

FIG. 7D is a schematic diagram showing how the near flexural area of the sigmoid colon is pushed up when the first bending portion of the insertion portion is bent in the U-direction from the condition in which the distal end of the insertion portion is located at the position shown in FIG. 7C and when the bending angle of the first bending portion is less than 90 degrees and the second bending portion maintains the straight state, out of the shown operation of the insertion portion wherein the endoscope system according to the first to third embodiments is used to insert the insertion portion of the endoscope to the far side (the side of the small intestine or stomach) of the large intestine;

FIG. 7E is a schematic diagram showing how the first bending portion of the insertion portion is bent beyond 90 degrees in the U-direction from the condition in which the distal end of the insertion portion is located at the position shown in FIG. 7C or FIG. 7D to bend the second bending portion in the same direction as the first bending portion so that the first bending portion is hooked to the near flexural area and the far side of the near flexural area is observed, out of the shown operation of the insertion portion wherein the endoscope system according to the first to third embodiments is used to insert the insertion portion of the endoscope to the far side (the side of the small intestine or stomach) of the large intestine;

FIG. 7F is a schematic diagram showing how the bending amount of the second bending portion is reduced by moving the distal end of the insertion portion from the near flexural area to a far flexural area when the bending amount of the first bending portion is reduced from the condition in which the distal end of the insertion portion is located at the position shown in FIG. 7E so that the bending amount of a first bending portion 34 is brought to a proper threshold angle (e.g. less than 25 degrees), out of the shown operation of the insertion portion wherein the endoscope system according to the first to third embodiments is used to insert the insertion portion of the endoscope to the far side (the side of the small intestine or stomach) of the large intestine;

FIG. 10 is a schematic block diagram showing the relation between components controlled by a control microcomputer in the endoscope system according to the third embodiment;

FIG. 11 is a flowchart showing how the endoscope system according to the third embodiment is used to insert the distal end of the insertion portion into the far side of the cavity of the winding tube by the operation similar to the operation according to the first embodiment; and FIG. 12 is a flowchart showing how the endoscope system according to the third embodiment is used to insert the distal end of the insertion portion into the far side of the cavity of the winding tube by the operation similar to the operation according to the second embodiment.

DETAILED DESCRIPTION OF THE INVENTION

Hereinafter, embodiments of this invention will be described with reference to the drawings.

The first embodiment is described with reference to FIG. 1 to FIG. 7G.

Figure 1:
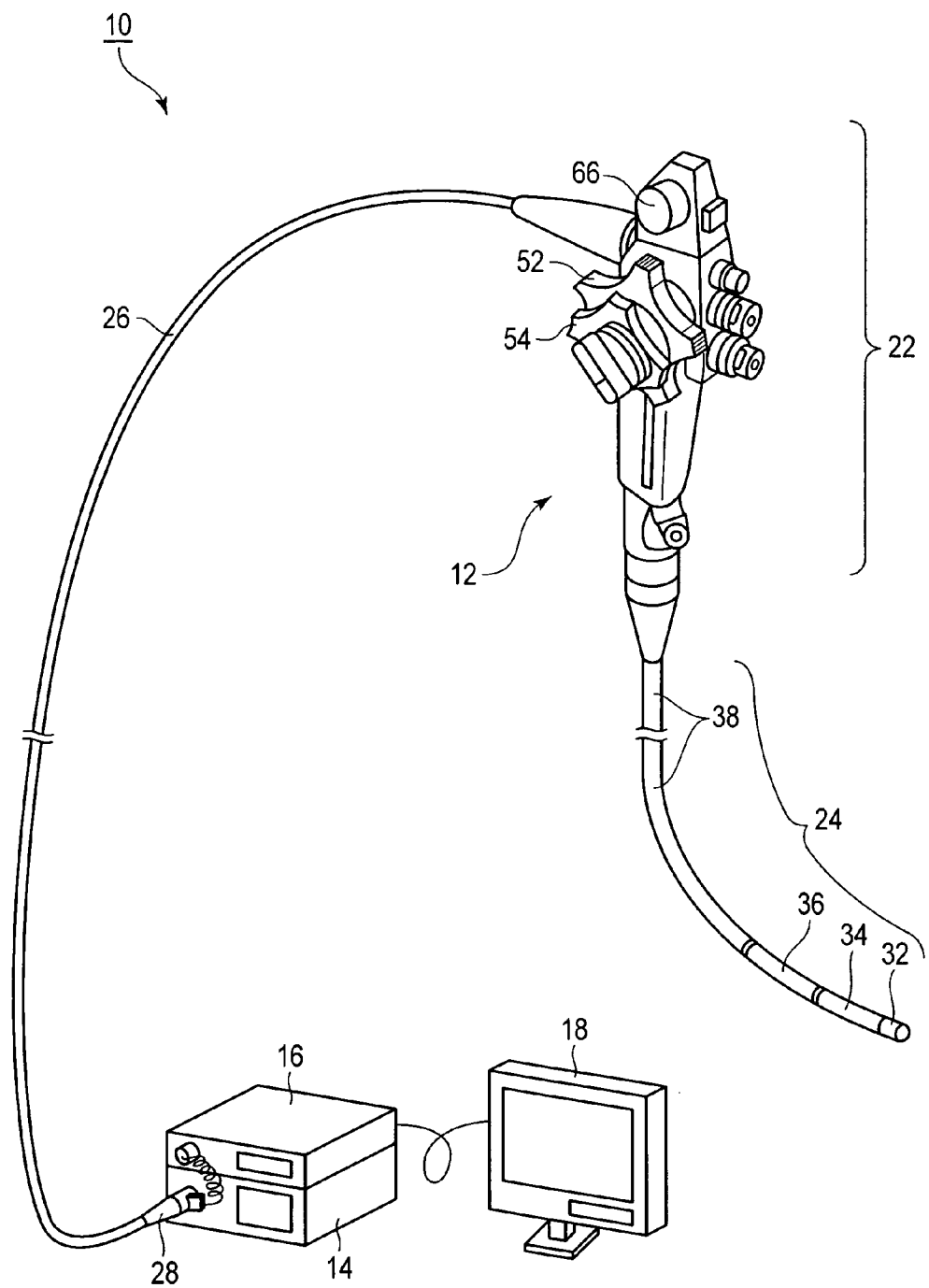
FIG. 1 is a schematic diagram showing an endoscope system according to first to third embodiments.

As shown in FIG. 1, an endoscope system 10 according to the first embodiment of the present invention includes an endoscope (endoscope body) 12 including an observation optical system (imaging means) and an illumination optical system (illumination means) that are not shown, a light source apparatus 14 which is removably connected to the endoscope 12 and which supplies illumination light to the endoscope 12, a video processor 16 which is removably connected to the endoscope 12 and which controls the observation optical system of the endoscope 12 and which processes a signal obtained from the observation optical system to output a standard video signal, and a monitor 18 which displays an endoscope image obtained by the signal processing in the video processor 16. An unshown image recording device, for example, can be connected to the video processor 16. The endoscope 12 may have therein a small light source such as an LED instead of the light source apparatus 14.

The endoscope 12 includes an operation portion (endoscope body) 22 which is gripped by a surgeon to enable the bending of later-described first and second bending portions 34 and 36, an elongated insertion portion 24 which extends from the operation portion 22 and which is inserted into an observation target part, a universal cord 26 which extends from the side surface of the operation portion 22 and which has therein, for example, a signal cable connected to the unshown observation optical system and a light guide for transmitting the illumination light, and a connector portion 28 which is provided at the end of the universal cord 26 and which is removably connected to the light source unit 14 and the video processor 16. In other words, the operation portion 22 is provided at the proximal end of the insertion portion 24.

The insertion portion 24 includes a distal rigid portion 32 provided at the distal end of the insertion portion 24, the bendable first bending portion 34 provided at the rear end of the distal rigid portion 32, the bendable second bending portion 36 provided at the rear end of the first bending portion 34, and a long and flexible tubular portion 38 which is provided at the rear end of the second bending portion 36 and which is made of a soft and tubular material. That is, the distal rigid portion 32, the first bending portion 34, the second bending portion 36, and the tubular portion 38 are arrayed in order from the distal side to the proximal side to form the insertion portion 24.

The distal rigid portion 32 has therein, for example, an imaging portion including an unshown solid-state image sensing device such as a CCD or a CMOS serving as the observation optical system and a circuit substrate for driving the solid-state image sensing device, and the unshown light guide as the illumination optical system which transmits the illumination light for illuminating the observation target part in a body cavity. Thus, it is possible to illuminate a subject with the illumination light from the distal face of the distal rigid portion 32, image the illuminated subject by the imaging portion, and display an image of the subject on the monitor 18.

As described above, in the present embodiment, the insertion portion 24 of the endoscope 12 includes the two bending portions 34 and 36: the first bending portion 34 located in the vicinity of the distal rigid portion 32, and the second bending portion 36 located in the vicinity of the tubular portion 38.

Figure 2:
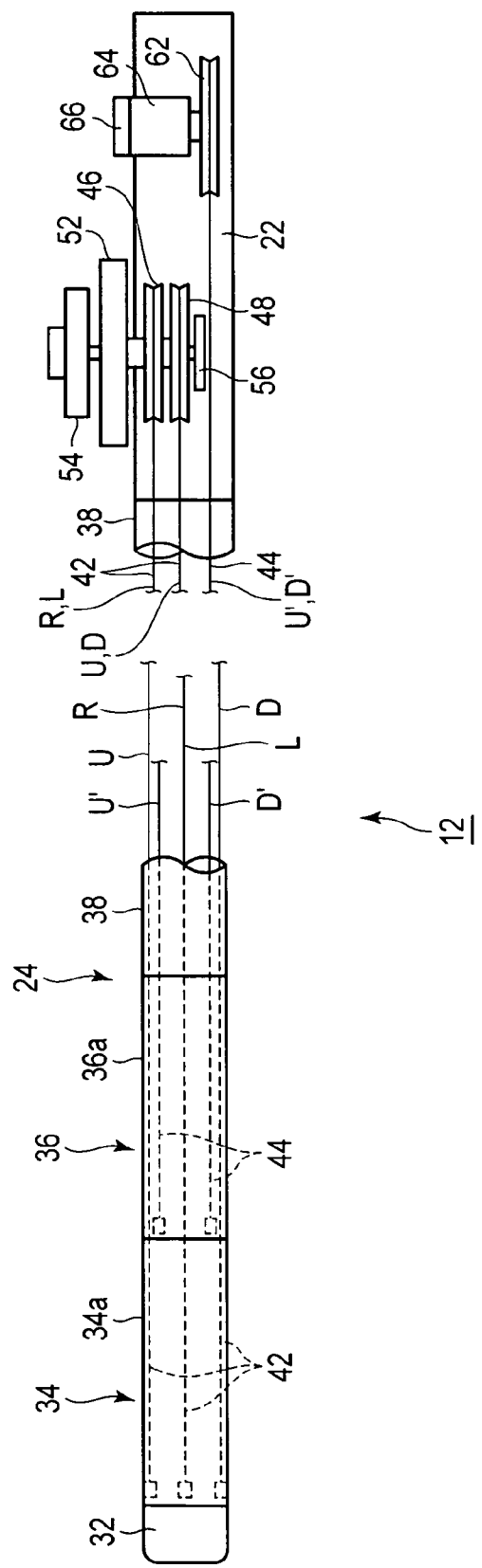
FIG. 2 is a schematic diagram showing the relation between a first bending portion of an insertion portion and first and second drums of an operation portion, and the relation between a second bending portion and a third drum of the operation portion of an endoscope in the endoscope system according to the first to third embodiments.
Figure 3A:
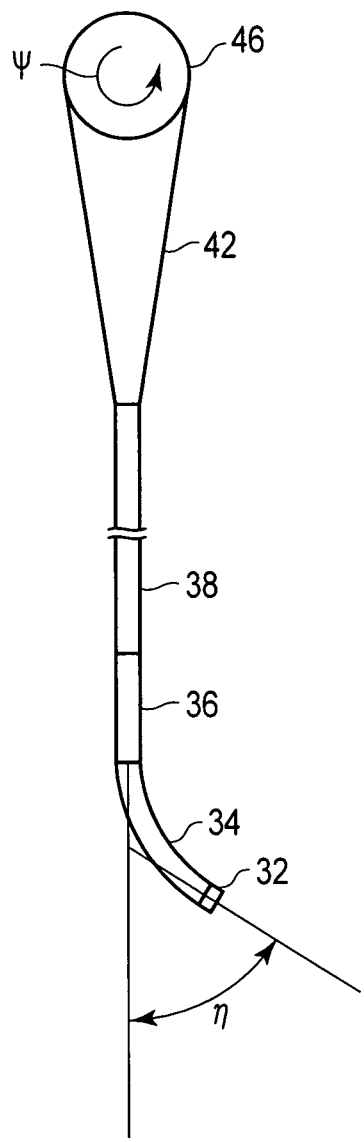
FIG. 3A is a schematic diagram showing a state in which the first bending portion is bent when the first drum of the operation portion of the endoscope is rotated in the endoscope system according to the first to third embodiments.

The first bending portion 34 and the second bending portion 36 shown in FIG. 2 respectively include bending tubes (first and second bending drive mechanisms) 34a and 36a each formed of a plurality of known bending pieces, braids provided outside the bending tubes, and outer tube provided outside the braids. For example, four angle wires (first bending drive mechanisms) 42 (U, D, R, and L) are fixed to the distal end of the curving tube 34a of the first bending portion 34 to correspond to the bending directions of the first bending portion 34. For example, two angle wires (second bending drive mechanisms) 44 (U' and D') are also fixed to the distal end of the bending tube 36a of the second bending portion 36. Therefore, the first bending portion 34 can be bent in the vertical (UP/DOWN) direction (indicated by U and D in FIG. 2) and in the horizontal (RIGHT/LEFT) direction (indicated by R and L in FIG. 2), and the second bending portion 36 can be bent in the vertical direction.

As shown in FIG. 2, the two angle wires 42 (U and D) for vertically bending the first bending portion 34 are wound around and fixed to a first drum (first bending drive mechanism) 46 inside the operation portion 22. The two angle wires 42 (R and L) for horizontally bending the first bending portion 34 are wound around and fixed to a second drum 48 inside the operation portion 22. The first and second drums 46 and 48 are coaxially located. A first angle knob (bending operation input portion) 52 for rotating the first drum 46 and a second angle knob 54 for rotating the second drum 48 are provided outside the operation portion 22. The first and second angle knobs 52 and 54 are coaxially located. The first and second drums 46 and 48 and the first and second angle knobs 52 and 54 are coaxially located. If the first angle knob 52 is rotated around its axis, the first drum 46 rotates around the same axis by the same angle as the first angle knob 52. If the second angle knob 54 is rotated around its axis, the second drum 48 rotates around the same axis by the same angle as the second angle knob 54. The bending tube 34a, the wires 42, and the first drum 46 form the first bending drive mechanism for bending the first bending portion 34.

In this embodiment, the position that allows the first bending portion 34 to be straight is defined as an initial position of the first angle knob 52, and the position that allows the second bending portion 36 to be straight is defined as an initial position of a motor 64. A rotatable angle of the first angle knob 52 in the U-direction (positive direction) and a D-direction (negative direction) and a bendable angle $\psi$ of the first and second bending portions 34 and 36 in the U-direction and the D-direction are preferably symmetric. In particular, the rotatable angle $\psi$ of the first angle knob 52 and the bendable angle $\psi$ of the first bending portion 34 are preferably, for example, about 180 degrees from the straight state (initial state) $\eta 0$ of the first bending portion 34 both in the U-direction and the D-direction. The rotatable angle of the second angle knob 54 and the bendable angle of the second bending portion 36 are preferably, for example, about 160 degrees from the straight state (initial state) of the first bending portion 34 both in an R-direction and an L-direction. A bendable angle $\theta$ of the second bending portion 36 is preferably, for example, about 120 degrees from the straight state (initial state) $\theta_0$ of the second bending portion 36 both in the U-direction and the D-direction.

A knob position detecting potentiometer (input amount detector) 56 for detecting the rotational position of the first drum 46 is attached to the first drum 46. This potentiometer 56 is disposed inside the operation portion 22. When the potentiometer 56 is set in accordance with an initial position (the position at which the first bending portion 34 is straight) of the first angle knob 52, the potentiometer 56 can detect the rotation amount of the first drum 46, that is, the rotational position (rotation angle) $\psi$ of the first angle knob 52. Thus, the potentiometer 56 detects, as a bending operation input amount, a bending operation amount input to the first angle knob (first curving operation input portion) 52. The rotation amount $\psi$ of the first angle knob 52 shown in FIG. 3A, that is, the rotation amount $\psi$ of the first drum 46 substantially corresponds to a bending amount (bending angle) $\eta$ of the first bending portion 34 in the U-direction and the D-direction. Accordingly, the bent state of the first bending portion 34 in the U- and D-directions can be estimated in accordance with the rotation amount of the first angle knob 52 by the use of the potentiometer 56.

As shown in FIG. 2, the two angle wires 44 (U' and D') for bending the second bending portion 36 in the U- and D-directions are wound around and fixed to a third drum (second bending drive mechanism) 62 inside the operation portion 22. The motor (driving unit) 64, and an encoder (rotational position detector) 66 which detects the rotation amount (rotation angle) $\omega$ (see FIG. 3B) of the motor (second bending drive mechanism) 64 are disposed in the third drum 62. The motor 64 generates driving force to bend the second bending portion 36. Thus, the bending tube 36a, the wires 44, the third drum 62, and the motor 64 form the second bending drive mechanism for bending the second bending portion 36.

Although the motor 64 and the encoder 66 shown in FIG. 1 and FIG. 2 partly project out of the operation portion 22, it is also preferable that the motor 64 and the encoder 66 are disposed inside the operation portion 22. It is also preferable that the motor 64 is disposed inside the insertion portion 24 rather than inside the operation portion 22.

As shown in FIG. 4A and FIG. 4B, the second angle wires 44 (U' and D') are previously provided with sags 44a and 44b. The wires 44 preferably have such a sag amount that the sags 44a and 44b slightly remain in the wires 44 (U' and D') even if the motor 64 is rotated to rotate the third drum 62 from a condition shown in FIG. 4A in which the third drum 62 and the motor 64 are at neutral positions (a condition in which the second bending portion 36 is straight) and bend the second bending portion 36 to a maximum bending angle in the U-direction as shown in FIG. 4B.

As will be described later, the wires 44 (U' and D') have the sufficient sags 44a and 44b even if the curved second bending portion 36 is in touch with a body wall. Therefore, the second bending portion 36 can be further bent in the U-direction or the amount of bending in the U-direction can be reduced by the sags 44a and 44b, so that the second bending portion 36 has play even when bent, and the second bending portion 36 is not forcibly curved in a reverse direction. Therefore, no great force is applied to the inner wall of a cavity of a tube. Although not shown, the first bending portion 34 and the angle wires 42 also have the similar configuration.

Figure 5:
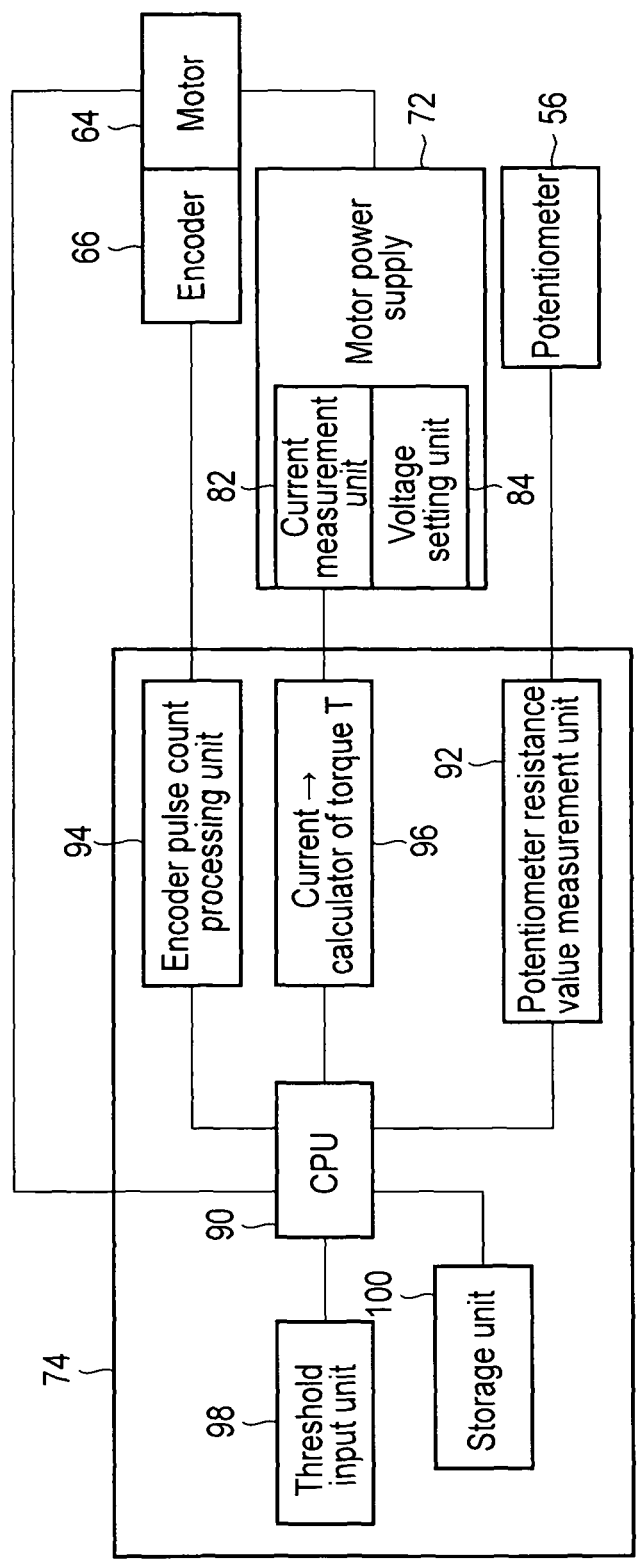
FIG. 5 is a schematic block diagram showing the relation between components controlled by a control microcomputer in the endoscope system according to the first and second embodiments.

For example, a motor power supply (torque amount detector, tension detector) 72 shown in FIG. 5 is disposed inside the operation portion 22, in addition to the potentiometer 56, the motor 64, and the encoder 66. A control microcomputer (controller) 74 shown in FIG. 5 which controls the potentiometer 56, the motor 64, the encoder 66, and the motor power supply 72 is disposed inside the operation portion 22.

The motor power supply 72 and the control microcomputer 74 are not exclusively provided inside the operation portion 22 of the endoscope 12, and are also suitably provided in, for example, one of the light source unit 14, the video processor 16, and the monitor 18. When the motor power supply 72 and the control microcomputer 74 are disposed in, for example, one of the light source unit 14, the video processor 16, and the monitor 18, the motor power supply 72 and the control microcomputer 74 are electrically connected to the potentiometer 56, the motor 64, and the encoder 66 via the universal cord 26.

That is, the endoscope 12 may include the control microcomputer (controller) 74, or the control microcomputer 74 may be provided outside the endoscope 12 (the endoscope system 10 has only to include the control microcomputer 74). The present embodiment is hereinafter described on the assumption that the control microcomputer (controller) 74 may be provided in the endoscope 12 or in one of the devices in the endoscope system 10 other than the endoscope 12. The case in which the control microcomputer 74 is connected to the endoscope 12 includes the case in which the endoscope 12 has the control microcomputer 74 and the case in which the control microcomputer 74 is provided outside the endoscope 12.

Similarly, the endoscope 12 may include the motor power supply 72, or the motor power supply 72 may be provided outside the endoscope 12 (the endoscope system 10 has only to include the motor power supply 72). The present embodiment is hereinafter described on the assumption that the motor power supply 72 may be provided in the endoscope 12 or in one of the devices in the endoscope system 10 other than the endoscope 12. The case in which the motor power supply 72 is connected to the endoscope 12 includes the case in which the endoscope 12 has the motor power supply 72 and the case in which the motor power supply 72 is provided outside the endoscope 12.

The motor power supply 72 includes a current measurement unit 82 which measures a current I running through the motor 64, and a voltage setting unit 84 which sets a voltage to be applied to the motor 64.

The control microcomputer 74 includes a CPU (controller) 90, a resistance value measurement unit 92 which measures the resistance value of the potentiometer 56, a count processing unit 94 which counts the pulse of the encoder 66, a torque calculator (torque amount detector) 96 which calculates generated torque T of the motor 64, a threshold input unit (setting portion) 98, and a storage unit 100.

The resistance value measurement portion 92, the count processing unit 94, the torque calculator 96, the threshold input portion 98, and the storage portion 100 are electrically connected to and controlled by the CPU 90. The motor 64 is also electrically connected to and controlled by the CPU 90.

Therefore, the resistance value of the potentiometer 56 is measured by the resistance value measurement unit 92 of the control microcomputer 74, so that the operation amount, that is, input amount (rotation angle) $\psi$ of the first angle knob 52 in the U- and D-directions can be obtained, and the bending amount of the first bending portion 34 in the U- and D-directions can be estimated. Thus, the resistance value measurement unit 92 of the control microcomputer 74 functions as a bending amount calculator which calculates the bending amount of the first bending portion 34 bent by the first bending drive mechanism (the angle wires 42 and the first drum 46). The count processing portion 94 of the control microcomputer 74 can process the counts of the encoder pulses by the encoder 66 to obtain the rotational position information (rotation angle) $\omega$ regarding the motor 64.

Here, when the torque T is calculated from the current amount of the motor 64, the relation between the current I running through the motor 64 and the output torque T of the motor 64 is represented by $T=km \cdot I$. km is a torque constant and is an eigenvalue for each motor 64. Therefore, the control microcomputer 74 can control the current I running through the motor 64 to calculate the torque T generated by the motor 64. That is, the control microcomputer 74 can calculate torque in accordance with the current I measured by the current measurement unit 82 of the motor power supply 72 and obtain the torque T generated by the motor 64.

The threshold input unit (threshold setting portion) 98 is used to set later-described threshold angles $\psi_0, \psi_1, \psi_2, \psi_3$ and $\psi_4$. The storage unit 100 can be used to store the threshold angles $\psi_0, \psi_1, \psi_2, \psi_3$ and $\psi_4$, and also store, for example, the operation amount (rotation angle) $\psi$ of the first angle knob 52 in the U- and D-directions, and the rotational position information (rotation angle) $\omega$ for the motor 64.

The rotation angle $\psi$ of the first angle knob 52 corresponds to the bending angle $\theta$ of the first curving portion 34. The rotation angle $\omega$ of the motor 64 corresponds to the bending angle $\theta$ of the second curving portion 36.

This embodiment is described on the assumption that the rotation angle $\psi$ of the first angle knob 52 corresponds or substantially corresponds to the curve angle $\eta$ of the first bending portion 34. When the rotation angle $\psi$ of the first angle knob 52 is rotated to, for example, 90 degrees from 0 degrees (straight state), the first curving portion 34 is also bent 90 degrees from straight state (0 degrees). The supporting point of the bending of the first curving portion 34 is the proximal end of the curving tube 34a of the first curving portion 34.

The rotation angle $\omega$ of the motor 64 corresponds or substantially corresponds to the curve angle $\theta$ of the second bending portion 36. When the motor 64 is controlled to rotate the rotation angle $\omega$ of the third drum 62 to, for example, 90 degrees from 0 degrees, the second bending portion 36 is also bent 90 degrees from the straight state. The supporting point of the bending of the second curving portion 36 is the proximal end of the curving tube 36a of the second curving portion 36.

The rotational position of the motor 64 of the endoscope 12 in a linear state (neutral state) $\theta_0$ in which the second bending portion 36 is straight without any load of external force is measured, and this position is set as a neutral position $\omega 0$. Torque $Tu_0$ necessary when the second bending portion 36 in the linear state without any load of external force is curved relative to the neutral state (angle $\theta_0$) by an angle $\theta_1$ (e.g. 15 degrees) in the U-direction is measured in advance. Torque $Td_0$ necessary to curve the second bending portion 36 by an angle $\theta_2$ (e.g. −15 degrees) in the D-direction is also measured in advance. The torques $Tu_0$ and $Td_0$ measured at this moment are stored in the storage portion 100 of the control microcomputer 74. The angle $\theta_1$ (15 degrees) and the angle $\theta_2$ (−15 degrees) are illustrative only, and proper angles can be set by the threshold input unit 98 within the rotatable angle of the second bending portion 36.

The voltage of the motor power supply 72 is set to cause the motor 64 to generate, for example, the torque $Tu_0$. PID control is known as a setting method used for this purpose. The PID control is a type of feedback control, and controls an input value by three elements: a deflection of an output value from a desired value, the integration thereof, and a derivation thereof. In the present embodiment, voltage information regarding the motor power supply 72 is an input value, torque information generated by the motor 64 is an output value, and torque information derived in the control microcomputer 74 is a desired value, whereby the PID control is applied, and voltage information to be supplied to the motor power supply 72 is derived. That is, the desired torque T of the motor 64 is generated by the control of the voltage of the motor power supply 72.

As will be described later, when the second curving portion 36 is directed to the neutral position (initial position) $\theta_0$ at a velocity $V_0$, the voltage information regarding the motor power supply 72 is an input value, a rotation velocity obtained from the rotational position information for the motor 64 is an output value, and velocity information derived in the control microcomputer 74 is a desired value, whereby the PID control is applied, and voltage information to be supplied to the motor power supply 72 is derived.

A value calculated by the time difference of the rotational position information for the motor 64 is used for the rotation velocity of the motor 64. A motor rotation velocity $V=X(t2)-X(t1)$, $t2>t1$, wherein $X(t2)$ is the rotational position of the motor 64 at a time $t2$, and $X(t1)$ is the rotational position of the motor 64 at a time $t1$.

Figure 6:
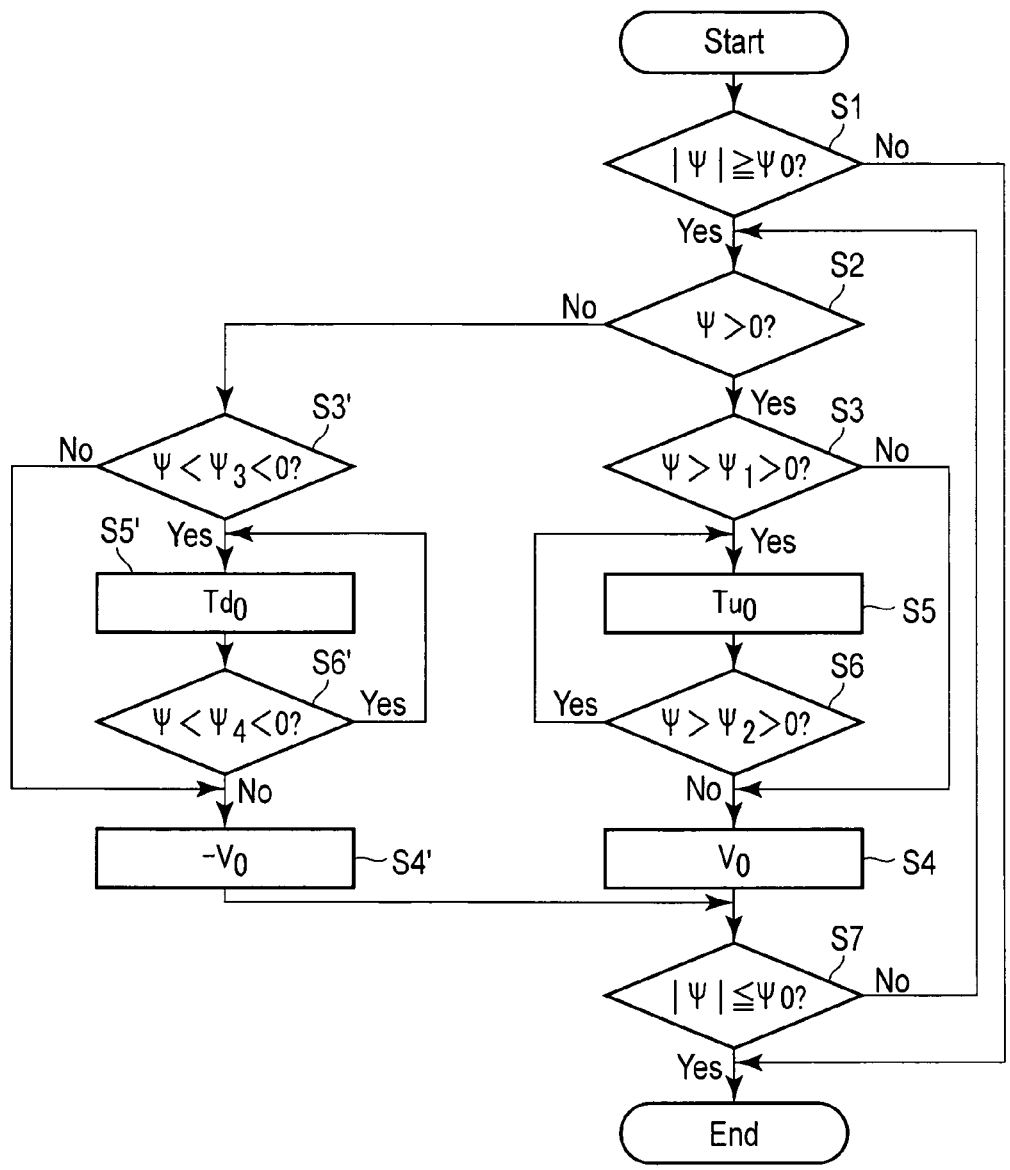
FIG. 6 is a flowchart showing how the endoscope system according to the first embodiment is used to insert the distal end of the insertion portion into the far side of a cavity of the winding tube.

A flowchart shown in FIG. 6 is used to describe below how the endoscope system 10 according to the present embodiment is used to bend the second bending portion 36 in the same direction as the bending direction of the first bending portion 34 by the use of the motor 64, the third drum 62, the wires 44, and the bending tube 36a which serve as the second bending drive mechanism when the first bending portion 34 is in a predetermined curved state. In the example described here, the first and second bending portions 34 and 36 are mainly moved in the upward direction (U-direction).

First, the threshold angles $\psi_0$ (e.g. 5 degrees), $\psi_1$ (e.g. 90 degrees), $\psi_2$ (e.g. 25 degrees), $\psi_3$ (e.g. −90 degrees) and $\psi_4$ (e.g. −25 degrees) are set by the threshold input unit 98. The threshold angle $\psi_0$ is preferably a given value between, for example, 0 degrees and, for example, 10 degrees.

Although the threshold angle $\psi_1$ of the angle $\psi$ of the first angle knob 52 in the U-direction detected by the potentiometer 56 is 90 degrees in the present embodiment described, the threshold angle $\psi_1$ is not limited to 90 degrees, and can be suitably set to, for example, 80 degrees or 120 degrees. The threshold angle $\psi_2$ is not limited to 25 degrees, and can be suitably set to, for example, 20 degrees or 30 degrees. The threshold angles $\psi_3$ and $\psi_4$ can also be suitably set. The threshold angle $\psi_1$ is greater than the threshold angle $\psi_2$, and the threshold angles $\psi_3$ is smaller the threshold angle $\psi_4$. As the threshold angles $\psi_3$ and $\psi_4$ are negative values, the absolute value of the threshold angle $\psi_3$ is higher than the absolute value of the threshold angle $\psi_4$.

If the first angle knob 52 is rotated in the U-direction or the D-direction from the initial position, the potentiometer 56 obtains the rotation angle $\psi$ of the first angle knob 52. The first angle knob 52 is then rotated in the U-direction, and the processing is started when the absolute value ($|\psi|$) of the rotation angle $\psi$ of the first angle knob 52 has become equal to or more than the predetermined threshold angle $\psi_0$ (e.g. 5 degrees), that is, when the operation to bend the first bending portion 34 is started (S1). Here, the CPU 90 and the storage portion 100 function as determination unit to determine the start of this processing. The CPU 90 and the storage portion 100 also function as the determination unit in judgments (S2, S3, S6, S7, S3', and S6') described below.

It can be determined that the rotation of the first angle knob 52 in the U-direction is started if the rotation angle $\psi$ is a positive value or that the rotation of the first angle knob 52 in the D-direction is started if the rotation angle $\psi$ is a negative value (S2). In the case described below, the rotation angle $\psi$ is a positive value, and the first angle knob 52 is rotated in the U-direction ($\psi>0$).

While the first angle knob 52 is being rotated in the U-direction, the potentiometer 56 obtains the rotation angle $\psi$ of the first angle knob 52 in the U-direction. It is judged whether the rotation angle $\psi$ of the first angle knob 52 in the U-direction is equal to or more than the threshold angle $\psi_1$ (e.g. 90 degrees) or is less than the threshold angle $\psi_1$ (S3). When the rotation angle $\psi$ is less than the angle $\psi_1$, the motor 64 is controlled (a bending drive signal is output to the motor 64 from the CPU 90) to bend the second bending portion 36 at the velocity $V_0$ (i.e. apply torque $Tu_1$) so that the second bending portion 36 will maintain the neutral state even if the second bending portion 36 is subjected to external force (S4). The torque $Tu_1$ does not need to be constant. The torque $Tu_1$ can prevent the second bending portion 36 from bending in the U-direction and bending in the D-direction. Therefore, when the rotation angle of the first angle knob 52 in the U-direction is more than 0 degrees and less than, for example, the angle $\psi_1$ (e.g. 90 degrees), the second bending portion 36 will maintain the straight state even if the second bending portion 36 is subjected to external force and thereby curved.

When the rotation angle $\psi$ of the first angle knob 52 obtained by the potentiometer 56 is equal to or more than the angle $\psi_1$ (e.g. 90 degrees), the bending drive signal is output to the motor 64 from the CPU 90 so that the motor 64 keeps generating the constant torque (torque to bend the second bending portion 36 15 degrees in the U-direction) $Tu_0$ to bend the second bending portion 36 in the U-direction (S5). That is, if the first bending portion 34 is bent a predetermined angle (90 degrees), the predetermined torque $Tu_0$ is continuously applied to the second bending portion 36. Thus, the second bending portion 36 is bent by the constant torque $Tu_0$ in the same U-direction as the first bending portion 34 via the third drum 62 and the wires 44.

After the rotation angle $\psi$ of the first angle knob 52 has once become equal to or more than the angle $\psi_1$ (e.g. 90 degrees), when the rotation angle $\psi$ of the first angle knob 52 is still equal to or more than the angle $\psi_2$ (e.g. 25 degrees) even if reduced (S6), the constant amount of torque $Tu_0$ is continuously generated by the motor 64. Thus, the second bending portion 36 is kept in a predetermined curved state and curved in the U-direction.

After the rotation angle $\psi$ of the first angle knob 52 has become equal to or more than the angle $\psi_1$ (e.g. 90 degrees), when the rotation angle $\psi$ of the first angle knob 52 is reduced to less than the angle $\psi_2$ (e.g. 25 degrees) (S6), the motor 64 is controlled (the bending drive signal is output to the motor 64 from the CPU 90) to reduce the bending amount ($\theta$) of the second curving portion 36 to the neutral position $\theta_0$ at the velocity $V_0$ (S4). In other words, after the rotation angle $\psi$ of the first angle knob 52 is set to be equal to or more than the angle $\psi_1$, when the rotation angle $\psi$ of the first angle knob 52 is reduced to less than the angle $\psi_2$ (S6), the motor 64 is controlled to reduce the bending amount $\theta$ of the second bending portion 36 by given torque $Tu_2$ (which does not need to be constant) which maintains the velocity $V_0$ and bring the second bending portion 36 closer to the straight state (neutral position) $\theta_0$ (S4).

The processing is ended when the absolute value $|\psi|$ of the rotation angle of the first angle knob 52 has reached the predetermined threshold angle (e.g. 5 degrees) $\psi_0$ (S7). The above-described processing is continued when the absolute value $|\psi|$ of the rotation angle of the first angle knob 52 is equal to or more than the predetermined angle $\psi_0$. That is, when the rotation angle $\psi$ of the first bending portion 34 is again set to be equal to or more than the angle $\psi_1$ (e.g. 90 degrees) (S3), the motor 64 generates the constant torque $Tu_0$ to bend the second bending portion 36 in the U-direction (S5).

The bending of the first bending portion 34 and the second bending portion 36 in the D-direction (the rotation angle $\psi<0$) is briefly described below. When the first bending portion 34 is bent in the D-direction after the first bending portion 34 is bent in the U-direction, the processing is once ended, and restarted along the flow shown in FIG. 6.

It is judged whether the rotation angle $\psi$ of the first angle knob 52 in the D-direction is equal to or less than the threshold angle $\psi_3$ (e.g. -90 degrees) or is more than the threshold angle $\psi_3$ (S3'). When the rotation angle $\psi$ is more than the angle $\psi_3$, the motor 64 is controlled to bend the second bending portion 36 at a constant velocity ($-V_0$ (a velocity in a direction opposite to the above-mentioned velocity $V_0$)) (i.e. apply torque $Td_1$) so that the second bending portion 36 will maintain the neutral state even if the second bending portion 36 is subjected to external force (S4'). The torque $Td_1$ does not need to be constant. The torque $Td_1$ can prevent the second bending portion 36 from bending in the U- and D-directions, and the second bending portion 36 will maintain the straight state.

When the rotation angle $\psi$ of the first angle knob 52 obtained by the potentiometer 56 is equal to or less than the angle $\psi_3$ (e.g. -90 degrees), the motor 64 generates the constant torque $Td_0$ to bend the second bending portion 36 in the D-direction (S5'). Thus, the second bending portion 36 is, bent by the constant torque $Td_0$ in the same D-direction as the first bending portion 34 via the third drum 62 and the wires 44.

After the rotation angle $\psi$ of the first angle knob 52 has once become equal to or less than the angle $\psi_3$ (e.g. -90 degrees), when the rotation angle $\psi$ of the first angle knob 52 is still equal to or less than the angle $\psi_4$ (e.g. -25 degrees) even if increased (S6'), the constant amount of torque $Td_0$ continuously generated by the motor 64. Thus, the second bending portion 36 is kept in a predetermined curved state and curved in the D-direction.

After the rotation angle $\psi$ of the first angle knob 52 has become equal to or less than the angle $\psi_3$ (e.g. -90 degrees), when the rotation angle $\psi$ of the first angle knob 52 is increased to more than the angle $\psi_4$ (e.g. -25 degrees) (S6'), the motor 64 is controlled to reduce the curve amount of the second curving portion 36 to the neutral position $\theta_0$ at the velocity ($-V_0$) (S4').

The processing is ended when the absolute value $|\psi|$ of the rotation angle $\psi$ of the first angle knob 52 has reached the predetermined angle (e.g. 5 degrees) $\psi_0$ (S7). The above-described processing is continued when the absolute value $|\psi|$ of the rotation angle $\psi$ of the first angle knob 52 is equal to or more than the predetermined angle $\psi_0$.

Thus, the second bending portion 36 maintains the straight state before the first angle knob 52 is rotated to bend the first bending portion 34 in a predetermined bending amount $\eta 1$ (e.g. 90 degrees). When the bending angle $\eta$ of the first bending portion 34 has exceeded the predetermined curve amount $\eta 1$ (e.g. 90 degrees), the second bending portion 36 can be curved in the same direction as the first bending portion 34. On the other hand, the second bending portion 36 can be straight when the bending angle $\eta$ of the first bending portion 34 is less than a predetermined bending angle $\eta 2$ (e.g. 25 degrees) before the bending angle $\eta$ of the first bending portion 34 exceeds the predetermined bending amount $\eta 1$ (e.g. 90 degrees) or after the bending angle $\eta$ of the first bending portion 34 has exceeded the predetermined bending amount $\eta 1$ (e.g. 90 degrees).

Therefore, in both cases in which the first curving portion 34 is curved in the U-direction and the D-direction, the second curving portion 36 is curved to predetermined curve amounts $\theta_1$ and $\theta_2$ from the initial position $\theta_0$, and the torques $Tu_0$ and $Td_0$ are continuously applied to the motor 64 to keep the second curving portion 36 curved to the predetermined curve amounts $\theta_1$ and $\theta_2$ when the rotation angle $\psi$ of the first angle knob 52 obtained by the potentiometer 56 is more than the absolute values of the thresholds (first thresholds) $\psi_1$ and $\psi_3$ set by the threshold input portion 98.

Thus, when the rotation amount (bending amount to bend the first bending portion 34) of the first angle knob 52 detected by the potentiometer 56 is more than the absolute values of the first threshold angles $\psi_1$ and $\psi_3$ set by the threshold input portion (setting portion) 98, the second bending portion 36 is bent to the predetermined bending amounts $\theta_1$ and $\theta_2$ from the initial position $\theta_0$ in the same direction as the first bending portion 34 which has bent in accordance with the rotation amount of the first angle knob 52, and the torques $Tu_0$ and $Td_0$ are continuously applied to the motor 64 to keep the second bending portion 36 bent to the predetermined bending amounts $\theta_1$ and $\theta_2$. Accordingly, the second bending portion 36 can be automatically bent in the same direction in conformity to the first bending portion 34 by the absolute values of the first threshold angles $\psi_1$ and $\psi_3$ set by the threshold input portion 98. Therefore, by always defining the bending direction of the second bending portion 36 as the same direction as the first bending portion 34, it is possible to prevent the first bending portion 34 from being unintentionally unhooked from a cavity of a tube, for example, a large intestine, and improve the performance of the insertion of the distal end of the insertion portion 24 into a far side.

When the first bending portion 34 is curved, the motor 64 applies $Tu_0$, $Td_0$, $Tu_1$, $Td_1$, $Tu_2$, and $Td_2$ to the wires 44 to prevent the second bending portion 36 from bending in a direction opposite to the bending direction of the first bending portion 34. This can further ensure that the curved first bending portion 34 is prevented from being unintentionally unhooked from, for example, the cavity of the tube.

After the rotation angle $\psi$ of the first angle knob 52 obtained by the potentiometer 56 has exceeded the absolute values of the thresholds (first thresholds) $\psi_1$ and $\psi_3$ set by the threshold input portion 98, the torques $Tu_2$ and $Td_2$ are applied to the motor 64 to keep the second bending portion 36 in the predetermined bending amounts $\theta_1$ and $\theta_2$ when the rotation angle $\psi$ is more than the absolute values of the thresholds (first thresholds) $\psi_2$ and $\psi_4$ which are less than the absolute values of the thresholds $\psi_1$ and $\psi_3$, or to return the second bending portion 36 to the initial position $\theta_0$ when the rotation angle $\psi$ is less than the absolute values of the thresholds (second thresholds) $\psi_2$ and $\psi_4$. Thus, when the bending amount of the first bending portion 34 is reduced, the curve amount of the second bending portion 36 can be reduced accordingly, so that the curved states of the two bending portions 34 and 36 can be easily adjusted.

The operation for inserting the distal end of the insertion portion 24 of the endoscope 12 operating in this way into a far side (the side of the small intestine or stomach) of a large intestine LI is described.

The surgeon holds the flexible tubular portion 38 of the insertion portion 24 with the right hand while gripping the operation portion 22 of the endoscope 12 with the left hand. In this condition, the surgeon inserts the distal end of the insertion portion 24 into the far side from an anus side through a lumen (cavity of the tube) of the large intestine LI while checking what is called an endoscope image on a screen of the monitor 18 and operating the first and second angle knobs 52 and 54 with the left hand at the same time.

Figure 7A:
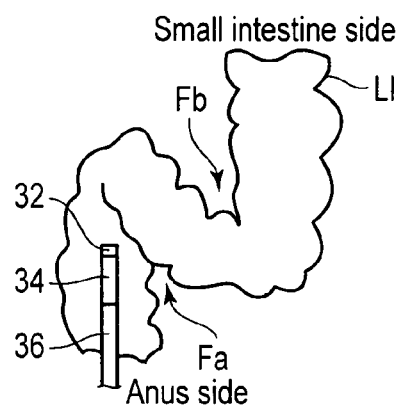
FIG. 7A is a schematic diagram showing a state in which the distal end of the insertion portion is inserted from an anus side toward a near flexural area of a sigmoid colon of a large intestine, out of the shown operation of the insertion portion wherein the endoscope system according to the first to third embodiments is used to insert the insertion portion of the endoscope to the far side (the side of a small intestine or stomach) of the large intestine.

For example, when the distal end of the insertion portion 24 of the endoscope 12 is inserted into the far side of a sigmoid colon having flexural areas Fa and Fb of the large intestine LI shown in FIG. 7A, the distal end of the insertion portion 24 is disposed in the near flexural area Fa.

Figure 7B:
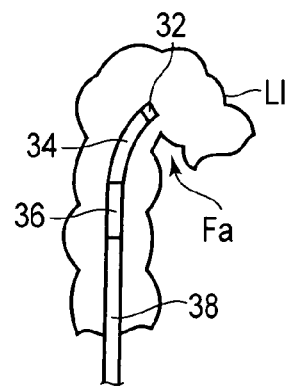
FIG. 7B is a schematic diagram showing the start of the bending of the first bending portion of the insertion portion in the U-direction from the condition in which the distal end of the insertion portion is located at the position shown in FIG. 7A, out of the shown operation of the insertion portion wherein the endoscope system according to the first to third embodiments is used to insert the insertion portion of the endoscope to the far side (the side of the small intestine or stomach) of the large intestine.

As shown in FIG. 7B, when the distal end of the insertion portion 24 is located in the flexural area Fa of the large intestine LI, the first angle knob 52 is rotated, for example, in the U-direction (see S1 and S2 in FIG. 6), and the first bending portion 34 of the insertion portion 24 is gradually bent in the U-direction (S3 in FIG. 6). In this case, the second bending portion 36 will maintain the straight state even if the inner wall of the large intestine LI collides with the second bending portion 36 (S3 and S4 in FIG. 6). That is, the curving of the second bending portion 36 in the D-direction is prevented, and the two bending portions 34 and 36 are prevented from being sigmoid as a whole.

Figure 7C:
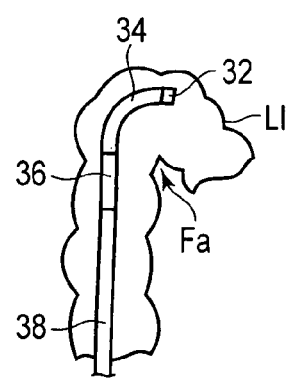
FIG. 7C is a schematic diagram showing the bending of the first bending portion of the insertion portion beyond 90 degrees in the U-direction from the condition in which the distal end of the insertion portion is located at the position shown in FIG. 7B, out of the shown operation of the insertion portion wherein the endoscope system according to the first to third embodiments is used to insert the insertion portion of the endoscope to the far side (the side of the small intestine or stomach) of the large intestine.

As shown in FIG. 7C, if the first bending portion 34 located in the flexural area Fa of the large intestine LI is curved beyond 90 degrees in the U-direction to move the distal end of the insertion portion 24 to the far side (S3 in FIG. 6), the second bending portion 36 maintains the straight state when the bending angle of the first bending portion 34 is less than 90 degrees. Therefore, as shown in FIG. 7D, the flexural area Fa of the large intestine LI is pushed up. Thus, the surgeon slowly and carefully performs a procedure without applying load to the large intestine LI.

As shown in FIG. 7E, the first bending portion 34 is bent 90 degrees in the U-direction (S3 in FIG. 6). The first bending portion 34 is bent 90 degrees in the U-direction for the purpose of ensuring that the first bending portion 34 is hooked to the flexural area Fa and observing the far side of the flexural area Fa. If the first bending portion 34 is bent 90 degrees or more in the U-direction, the second bending portion 36 is bent in the same U-direction as the first curving portion 34 (S5 in FIG. 6). Thus, the distal end of the insertion portion 24 of the endoscope 12 moves toward the flexural area Fb on the far side of the flexural area Fa. At the same time, the second bending portion 36 moves toward the flexural area Fb on the far side of the flexural area Fa if the second bending portion 36 is bent, so that the flexural area Fa of the large intestine LI is less pushed up by the first bending portion 34. As a result, the distal end of the insertion portion 24 automatically moves toward the far side of the large intestine LI. At the same time, as the flexural area Fa is firmly held by the first and second bending portions 34 and 36, the large intestine LI can be drawn closer by pulling the insertion portion 24 to the near side.

Figure 7G:
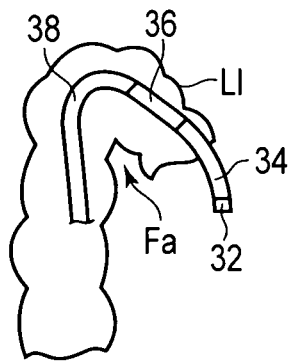
FIG. 7G is a schematic diagram showing how the distal end of the insertion portion is moved to the far flexural area of the large intestine from the condition in which the distal end of the insertion portion is located at the position shown in FIG. 7F and a flexible tubular portion of the insertion portion is bent to be passed through the near flexural area, out of the shown operation of the insertion portion wherein the endoscope system according to the first to third embodiments is used to insert the insertion portion of the endoscope to the far side (the side of the small intestine or stomach) of the large intestine.

When the curve amount of the first bending portion 34 is 90 degrees or more, the inner wall located in the vicinity of the near flexural area Fa is observed rather than the far flexural area Fb of the large intestine LI. Therefore, the curve amount of the first bending portion 34 is reduced to observe the flexural area Fb on the far side of the large intestine LI. If the first bending portion 34 is at 25 degrees or more when the bending amount of the first bending portion 34 is reduced, the second bending portion 36 maintains the curved state similar to the curved state when the distal end of the insertion portion 24 of the endoscope 12 moves toward the flexural area Fb on the far side of the flexural area Fa (S6 in FIG. 6). When the curve amount of the first bending portion 34 is less than 25 degrees, the distal end of the insertion portion 24 of the endoscope 12 is moved toward the flexural area Fb on the far side of the flexural area Fa as shown in FIG. 7F so that the curve amount of the second bending portion 36 is reduced at the velocity $V_0$ (S6 and S7 in FIG. 6). Thus, as shown in FIG. 7G, the first bending portion 34 and the second bending portion 36 are brought closer to the straight state, and the distal end of the insertion portion 24 can be easily moved to the flexural area Fb on the far side of the large intestine LI. At the same time, the flexible tubular portion 38 passes through the flexural area Fa of the large intestine LI, and is therefore bent.

By repeatedly operating the first and second angle knobs 52 and 54 to move the first bending portion 34 in four directions and cause the second bending portion 36 to suitably conform to the first bending portion 34, the distal end of the insertion portion 24 of the endoscope 12 is gradually moved toward the far side of the large intestine LI.

As shown in FIG. 7D, when the first bending portion 34 is bent to nearly push up the large intestine LI, the second bending portion 36 is automatically bent in conformity to the first bending portion 34 as shown in FIG. 7E if the bending angle of the first bending portion 34 has exceeded the threshold angles $\psi_1$ (e.g. 90 degrees). Therefore, it is possible to minimize the load applied to the large intestine LI by the insertion portion 24 of the endoscope 12.

In this way, the endoscope system 10 according to the present embodiment can assist the insertion of the distal end of the insertion portion 24 of the endoscope 12 into the far side of the cavity of the winding tube. Therefore, if the endoscope system 10 according to the present embodiment is used, the second bending portion 36 is automatically bent or maintains the straight state in conformity to the operation of the first angle knob 52 by the surgeon, that is, in conformity to the bending operation of the first bending portion 34. Therefore, the operation of inserting the insertion portion 24 of the endoscope 12 into the far side of the cavity of the tube by the surgeon can be assisted. Thus, the surgeon (operator) can more easily operate the endoscope 12 even in the case of a procedure that causes difficulty in the insertion into the far side of the cavity of the tube such as the large intestine LI, so that the fatigue of the surgeon can be reduced. Moreover, the surgeon (operator) can more easily insert the insertion portion 24, and the time required to insert the distal end of the insertion portion 24 from the anus side toward the stomach or the small intestine can therefore be reduced, so that a patient who has the large intestine observed by the use of the endoscope 12 feels less pain.

When the first bending portion 34 is bent in the U-direction, the second bending portion 36 can be kept straight or bent in the U-direction, and the bending of the second bending portion 36 in the D-direction is prevented. Therefore, for example, in order to insert the distal end of the insertion portion 24 into the far side of the large intestine LI, the first bending portion 34 is bent nearly 180 degrees in the U-direction to hook the first bending portion 34 to the flexural area Fa of the large intestine LI. In this condition, it is possible to prevent the first bending portion 34 from being unhooked from the flexural area Fa due to the unintentional bending of the second bending portion 36 in the D-direction.

Although the second bending portion 36 is only bent in the two directions, i.e. the U-direction and the D-direction in the present embodiment described, the second bending portion 36 can also be configured to bend in four directions. When the first bending portion 34 is bent, for example, between the U-direction and the R-direction, the second bending portion 36 can be bent between the U-direction and the R-direction if the flowchart shown in FIG. 6 is extended to the case in which the first bending portion 34 is bent in the R-direction and the L-direction.

Now, the second embodiment is described with reference to FIG. 8 and FIG. 9. This embodiment is a modification of the first embodiment, and the same components as the components described in the first embodiment or the components having the same functions are indicated by the same reference signs, and are not described in detail.

In this embodiment, bending in the U-direction is described as in the first embodiment, and bending in the D-direction is omitted.

The relation between the rotation amount of the motor 64 and the bending angle $\theta$ of the second bending portion 36 is acquired in advance in the second bending portion 36 of the insertion portion 24 of the endoscope 12 in the straight state (the rotation angle $\omega 0$ of the motor 64, and the bending angle $\theta_0$ of the second bending portion 36) without any load of external force. The relation between the rotation amount of the motor 64 and the curve angle $\theta$ of the second bending portion 36 is acquired because the rotation amount of the motor 64 and the bending angle $\theta$ of the second bending portion 36 may not be proportional to each other in some cases. The bending angle $\theta$ of the second bending portion 36 can be estimated from the rotation amount of the motor 64 by acquiring the relation between the rotation amount of the motor 64 and the bending angle $\theta$ of the second bending portion 36, and this bending angle is used as the estimated bending angle $\theta$.

The rotation amount of the motor 64 can be acquired by the encoder 66 provided in the motor 64, and is calculated by the count processing unit 94 of the encoder pulse of the control microcomputer 74.

The relation between the torque T and the estimated bending angle $\theta$ of the second bending portion 36 when the torque T of the motor 64 is slowly increased to bend, in the U-direction, the second bending portion 36 of the endoscope 12 in the straight state without any load of external force is then acquired. Here, the torque T of the motor 64 is calculated by the use of the current I passed through the motor 64. An example of the acquired relation is indicated by a broken line in FIG. 8. This broken line is proximate to $T=\alpha \cdot \theta + Tr$. $\alpha$ is the gradient of the bending angle $\theta$ of the second bending portion 36 relative to the actual torque T of the motor 64, and Tr (real) is the intercept when the estimated bending angle $\theta$ of the second bending portion 36 is 0 degrees. This is defined as Equation (1) and stored in the storage portion 100.

When the estimated bending angle $\theta$ of the second bending portion 36 is small, the torque amount of the motor 64 greatly changes. The torque amount of the motor 64 in this range is used, for example, for the starting resistance of the motor 64 and the friction of the wires 44. Therefore, Tr in Equation (1) is an estimated value. The torque T necessary to bend the second bending portion 36 a given angle $\theta$ can be calculated by Equation (1).

In the meantime, an equation to calculate torque T smaller than that in Equation (1) when the same angle $\theta$ is substituted can be represented by $Tu=\beta \cdot \theta + Ti$. This equation is set as Equation (2) by the setting portion 98, and stored in the storage portion 100. The gradients $\alpha$ and $\beta$ preferably have the same value so that Equation (1) and Equation (2) are parallel to each other, and the intercept Tr is slightly greater than Ti (imaginary). That is, the intercept Ti in Equation (2) is set to be slightly smaller than the intercept Tr in Equation (1).

Figure 9:
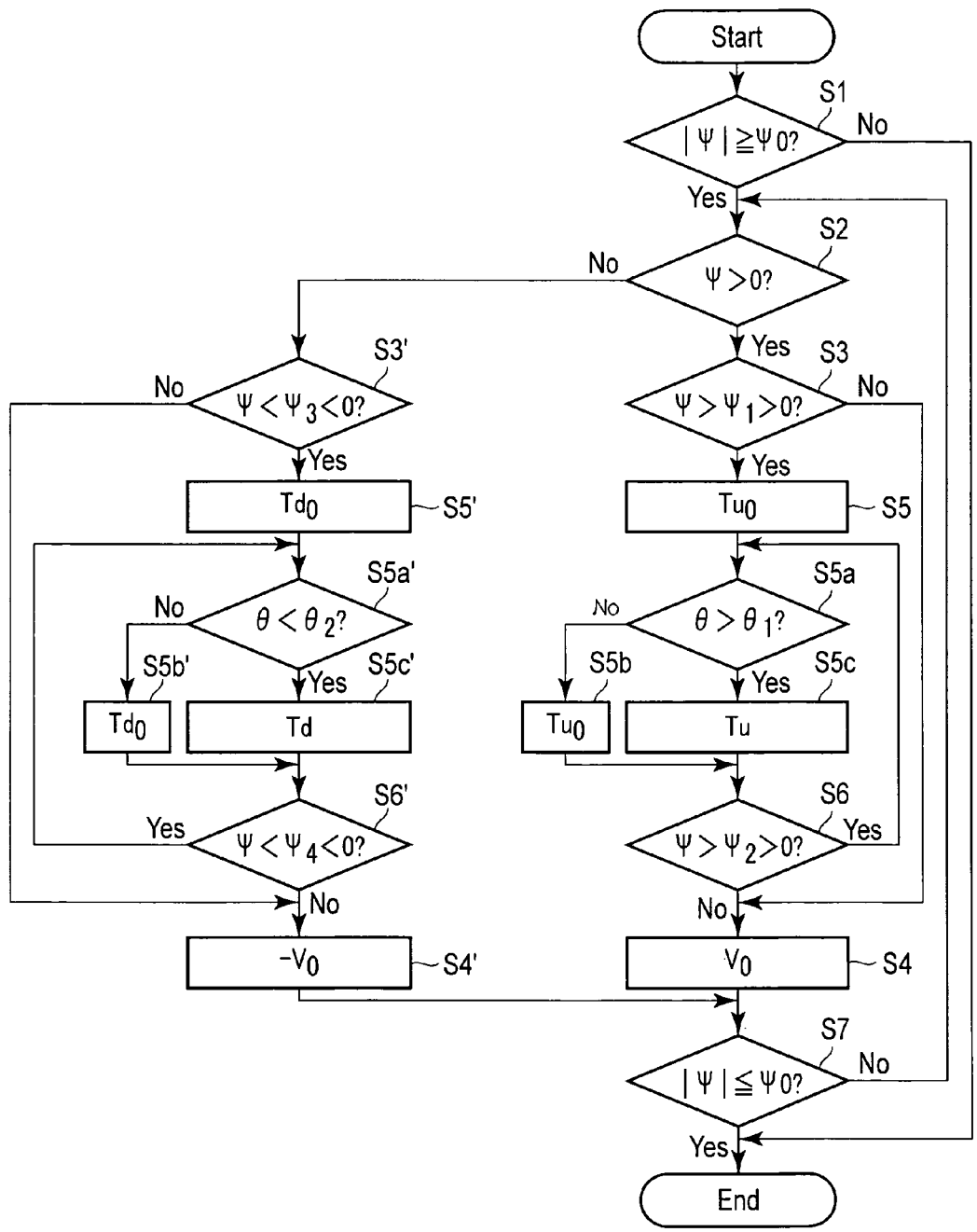
FIG. 9 is a flowchart showing how the endoscope system according to the second embodiment is used to insert the distal end of the insertion portion into the far side of the cavity of the winding tube.

A flowchart shown in FIG. 9 is used to describe below how the endoscope system 10 according to the present embodiment is used to bend the second bending portion 36 in the same direction as the bending direction of the first bending portion 34 when the first bending portion 34 is in a predetermined bent state. In the example described here, the first and second bending portions 34 and 36 are mainly moved in the upward direction (U-direction).

As in the flowchart shown in FIG. 6 according to the first embodiment, when the first angle knob 52 is at $\psi_1$ or more (e.g. 90 degrees) (S3), the motor 64 continuously generates a constant torque (torque to bend the second bending portion 36 15 degrees in the U-direction) $Tu_0$ to bend the second bending portion 36 in the U-direction (S5). Thus, the second bending portion 36 is bent by the constant torque $Tu_0$ in the same U-direction as the first bending portion 34 via the third drum 62 and the wires 44.

The estimated bending angle $\theta$ of the second bending portion 36 is then acquired by the rotation amount of the motor 64 for bending the second bending portion 36 in the U-direction, and this angle is substituted in Equation (2) to calculate the torque Tu.

When the estimated bending angle $\theta$ of the second bending portion 36 is smaller than $\theta_1$ (e.g. 15 degrees) (S5a), the motor 64 keeps directly applying the torque $Tu_0$ to the third drum 62 (S5b), thereby increasing the bending angle of the second bending portion 36 in the U-direction. When the estimated bending angle $\theta$ of the second bending portion 36 has reached $\theta_1$ (e.g. 15 degrees), the bending angle $\theta$ of the second bending portion 36 stops at $\theta_1$ (e.g. 15 degrees) if no external force is applied to the second bending portion 36. So far, the flow is the same as that described in the first embodiment.

In this case, the estimated bending angle $\theta$ increases if external force is applied to the second bending portion 36, for example, from the D-direction to the U-direction. When the estimated bending angle $\theta$ has reached $\theta_1$ (e.g. 15 degrees) or more, the motor 64 applies the torque Tu to the third drum 62 in accordance with Equation (2) (S5c).

In this case, if external force is continuously applied, the estimated bending angle $\theta$ is increased by the external force. Thus, the motor 64 keeps applying the torque Tu to the third drum 62 in accordance with Equation (2). On the other hand, if the external force is eliminated, the second bending portion 36 maintains the bent state when the external force is eliminated.

Here, in order to increase the bending angle of the second bending portion 36 in the U-direction, the amount of pushing into, for example, the cavity of the tube having a crooked region needs to be increased to apply external force to the second bending portion 36. If the bending angle of the second bending portion 36 is increased, the torque of the motor 64 necessary to bend the second bending portion 36 needs to be gradually increased. In the present embodiment, the torque Tu represented by Equation (2) which is slightly smaller than the torque T for the estimated bending angle of the second bending portion 36 represented by Equation (1) is applied to the motor 64. Therefore, if external force is applied, the difference of torque between Equation (1) and Equation (2) is reduced. When external force more than the torque of the difference between Equation (1) and Equation (2) is exerted, the second bending portion 36 can be bent in the U-direction. When external force less than the torque of the difference between Equation (1) and Equation (2) is exerted, the bent state of the second bending portion 36 can be maintained. Therefore, when the external force more than the torque of the difference between Equation (1) and Equation (2) is continuously exerted, the second bending portion 36 continues bending to the maximum bending amount.

Furthermore, as in the first embodiment, after the rotation angle ψ of the first angle knob 52 has once become equal to or more than, for example, $ψ_1$ (e.g. 90 degrees), the constant amount of torque $Tu_0$ is continuously generated by the motor 64 when the rotation angle ψ of the first angle knob 52 is still equal to or more than $ψ_2$ (e.g. 25 degrees) even if reduced (S6). On the other hand, after the rotation angle ψ of the first angle knob 52 has become equal to or more than the angle $ψ_1$ (e.g. 90 degrees), the motor 64 is controlled to reduce the bending amount of the second bending portion 36 to the neutral position $θ_0$ at the velocity $V_0$ when the rotation angle ψ of the first angle knob 52 is reduced to less than $ψ_2$ (e.g. 25 degrees) (S4).

The processing is ended when the absolute value |ψ| of the rotation angle of the first angle knob 52 has reached the predetermined threshold angle (e.g. 5 degrees) $ψ_0$ (S7). The above-described processing is continued when the absolute value |ψ| of the rotation angle of the first angle knob 52 is equal to or more than the predetermined angle $ψ_0$.

To bend the first bending portion 34 in the D-direction in the flowchart shown in FIG. 9, the angle is only negatively set, and the operation is similar, so that the explanation is omitted.

Figure 8:
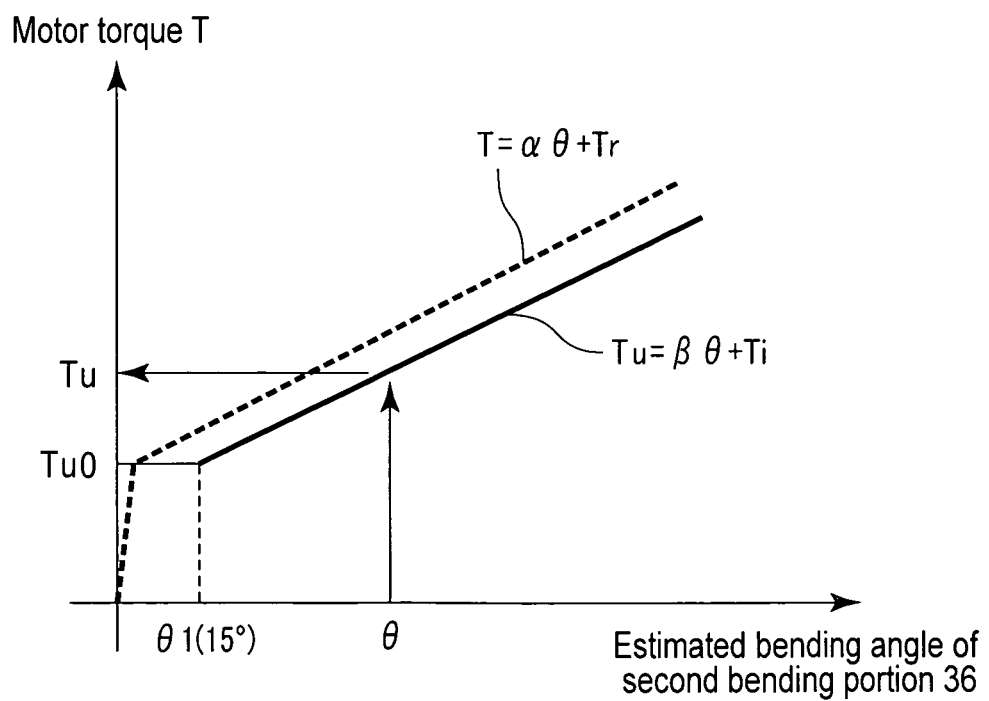
FIG. 8 is a schematic diagram wherein a broken line indicates the relation between torque and the estimated bending angle of the second bending portion and also indicates Equation (1) derived from this relation, when the endoscope system according to the second embodiment is used to slowly increase the torque of a motor so that the second bending portion of the endoscope in a linear state (initial state) without any load of external force is bent in the U-direction, and wherein a solid line indicates a line segment drawn in accordance with Equation (2) in which the same gradient is set so that torque smaller than the torque in Equation (1) is calculated when the same angle is substituted.

As shown in FIG. 8, when the second bending portion 36 is bent, the motor 64 is driven by the great torque Tu in accordance with the bending amount θ of the second bending portion 36. Therefore, when external force is applied to the second bending portion 36, difference torque (the difference of Equation (1)-Equation (2)) to maintain the curved state of the second bending portion 36 is reduced, so that it is possible to more quickly resist the external force when applied to the second bending portion 36. Thus, as the first and second bending portions 34 and 36 can be bent, for example, along the shape of the cavity of the tube, the operator of the endoscope 12 can more easily insert the first bending portion 34 into the cavity of the tube.

The operation of inserting the distal end of the insertion portion 24 of the endoscope 12 operating in this way to the far side of the large intestine LI is described.

When the distal end of the insertion portion 24 of the endoscope 12 is inserted into the far side of a sigmoid colon of the large intestine LI shown in FIG. 7A, the distal end of the insertion portion 24 is disposed in the near flexural area Fa.

As shown in FIG. 7B, when the distal end of the insertion portion 24 is located in the flexural area F of the large intestine LI, the first angle knob 52 is rotated, for example, in the U-direction, and the first bending portion 34 of the insertion portion 24 is gradually bent in the U-direction (S1 to S3). In this case, the second bending portion 36 will maintain the straight state even if the inner wall of the large intestine LI collides with the second bending portion 36 (S4). That is, the bending of the second bending portion 36 in the D-direction is prevented, and the two bending portions 34 and 36 are prevented from being sigmoid as a whole.

As shown in FIG. 7C, if the first bending portion 34 located in the flexural area F of the large intestine LI is bent 90 degrees in the U-direction to move the distal end of the insertion portion 24 to the far side, the flexural area Fa of the large intestine LI is pushed up, as shown in FIG. 7D. Thus, the surgeon slowly and carefully performs a procedure without applying load to the large intestine LI.

As shown in FIG. 7E, if the first bending portion 34 is bent 90 degrees or more in the U-direction, the second bending portion 36 is bent in the same U-direction as the first bending portion 34. Thus, the distal end of the insertion portion 24 of the endoscope 12 moves to the far side of the flexural area Fa. If, for example, the surface of the second bending portion 36 on the side of the D-direction collides with the inner peripheral surface of the large intestine LI, the second bending portion 36 is subjected to external force from the inner peripheral surface of the large intestine LI. When the estimated bending angle θ of the second bending portion 36 has become equal to or more than a predetermined angle $θ_1$ (e.g. 15 degrees), the motor 64 applies the torque Tu higher than the torque $Tu_0$ to the third drum 62. Thus, if the first bending portion 34 and the second bending portion 36 nearly push up the large intestine LI, great torque is gradually applied to the second bending portion 36 to increase the bending angle of the second bending portion 36 so that the second bending portion 36 will move away from the inner wall of the large intestine LI. On the other hand, if the surface of the second bending portion 36 on the side of the D-direction moves away from the inner wall of the large intestine LI, the bent state of the second bending portion 36 is maintained. That is, external force is applied to the surface of the second bending portion 36 on the side of the D-direction by combining the operation in which the first angle knob 52 is operated to bend the first bending portion 34 in the U-direction and push the insertion portion 24 into the far side. Therefore, the distal end of the insertion portion 24 can be inserted along the shape of the large intestine LI.

If the first bending portion 34 is at 90 degrees or more when the bending amount of the first bending portion 34 is reduced to observe the flexural area Fb on the far side of the large intestine LI, the second bending portion 36 maintains the curved state similar to the curved state when the distal end of the insertion portion 24 of the endoscope 12 moves to the far side of the flexural area Fa. When the bending amount of the first bending portion 34 is less than 25 degrees, the distal end of the insertion portion 24 of the endoscope 12 is moved to the far side of the flexural area Fa as shown in FIG. 7F so that the bending amount of the second bending portion 36 is reduced at the velocity $V_0$. Thus, as shown in FIG. 7G, the first bending portion 34 and the second bending portion 36 are brought closer to the straight state, and the distal end of the insertion portion 24 can be easily moved to the far side of the large intestine LI. At the same time, the flexible tubular portion 38 passes through the flexural area Fa of the large intestine LI, and is therefore bent.

Thus, by repeatedly moving the first bending portion 34 in four directions and causing the second bending portion 36 to suitably conform to the first bending portion 34, the distal end of the insertion portion 24 of the endoscope 12 is moved toward the far side of the large intestine LI.

As shown in FIG. 7D, if the first bending portion 34 is bent to nearly push up the large intestine LI, the second bending portion 36 is bent by reaction force from the inner wall of the large intestine LI in conformity to the first bending portion 34 as shown in FIG. 7E, so that it is possible to prevent the large intestine LI from being pushed up. Therefore, it is possible to prevent heavy load from being applied to the inner wall of the large intestine LI.

When external force is applied to the second bending portion 36, the second bending portion 36 is adjusted to the straight state or to be bent in the U-direction if the first bending portion 34 is bent in the U-direction. However, when the second bending portion 36 is subjected to external force from the U-direction, it is possible to prevent great force from rapidly applied to the second bending portion 36 because the wires 44 have the sags 44a and 44b.

Now, the third embodiment is described with reference to FIG. 10 to FIG. 12. This embodiment is a modification of the first and second embodiments, and the same components as the components described in the first and second embodiments or the components having the same functions are indicated by the same reference signs, and are not described in detail.

The relation between the current I running through the motor 64 and the output torque T of the motor 64 can be represented by T=km·I as described above. The conversion of the torque T of the motor 64 to tension F of the wires 44 can be represented by T=F·r, wherein r is the radius of the third drum 62. Therefore, the calculator 96 of the torque T in the control microcomputer 74 shown in FIG. 5 can be replaced by a calculator (tension detector) of the tension F, as shown in FIG. 10.

Thus, similar control can be performed, for example, by replacing the torque $Tu_0$ in the flowchart shown in FIG. 6 according to the first embodiment with tension $Fu_0$ and replacing the torque $Td_0$ with tension Fd0 (see FIG. 11). In the same manner, similar control can be performed by replacing the torque $Tu_1$ with tension $Fu_1$, replacing the torque $Td_1$ with tension Fd1, replacing the torque $Tu_2$ with tension $Fu_2$, and replacing the torque $Td_2$ with tension $Fd_2$.

In the same manner, similar control can be performed by replacing the torque $Tu_0$ in the flowchart shown in FIG. 9 according to the second embodiment with tension $Fu_0$, replacing the torque $Td_0$ with tension Fd0, replacing the torque Tu with tension Fu, and replacing the torque Td with tension Fd (see FIG. 12).

Although the torque T of the motor 64 is calculated to perform various kinds of control in the first and second embodiments described above, a tension sensor (not shown) that uses the tension F of the wires 44 may be used, or control that uses both the torque T of the motor 64 and the tension F of the wires 44 may be performed, instead of the calculation of the torque T of the motor 64.

Moreover, instead of the first angle knob 52, a joystick, for example, may be used to operate the first bending portion 34 (input an operation amount). In this case, the first drum 46 is rotated by an unshown motor.

[Addition]

An endoscope is characterized by comprises:

an insertion portion which includes a first curving portion and a second curving portion provided on the proximal side of the first curving portion;

an operation portion which is provided on the proximal side of the insertion portion, which includes a first curving operation input portion configured to input a curving operation to curve the first curving portion;

an input amount detector which is configured to detect, as a curving operation input amount, the curving operation input to the first curving operation input portion;

a first curving drive mechanism which is configured to curve the first curving portion to a curve amount corresponding to the curving operation input amount;

a curve amount calculator which is configured to calculate a curve amount of the first curving portion driven to curve by the first curving drive mechanism;

a second curving drive mechanism which curves the second curving portion;

a driving portion which is coupled to the second curving drive mechanism and which is configured to generate driving force to drive the second curving drive mechanism;

a setting portion which is configured to set a first threshold stored in advance and being compared with the curve amount of the first curving portion;

a determination portion which is configured to determine whether the curve amount of the first curving portion calculated by the curve amount calculator is more than the first threshold; and a controller which is configured to continuously output, to the driving portion, a curving drive signal that drives the second curving drive mechanism to curve the second curving portion in the same direction as the curving direction of the first curving portion when the determination unit determines that the curve amount of the first curving portion is more than the first threshold.

Thus, when the first curving portion is curved in a predetermined amount, it is judged that the first curving portion is hooked to a crooked region, and the second curving portion is curved. Accordingly, the distal end of the first curving portion is inserted into the far side of the cavity of the tube, that is, moves to the far side. As a result, the performance of the insertion of the distal end of the insertion portion into the far side can be improved.

That is, this endoscope further ensures the insertion of an insertion portion into the cavity of the tube having a crooked region such as a large intestine.

Preferably, the second curving drive mechanism includes a wire which connects the driving unit and the second curving portion, and the driving unit applies torque to the wire to prevent the second curving portion from curving in a direction opposite to the curving direction of the first curving portion.

This can further ensure that the first curving portion is prevented from being unintentionally unhooked from a cavity of the tube such as a large intestine.

Preferably, the second curving drive mechanism includes a wire which connects the driving unit and the second curving portion, and the driving unit is configured to apply torque to the wire to return the second curving portion to the initial position when the input amount of the input amount detector is reduced to less than the absolute value of a second threshold which is less than the absolute value of the first threshold after the input amount of the input amount detector has exceeded the absolute value of the first threshold.

Thus, when the curve amount of the first curving portion is reduced, the curve amount of the second curving portion can be reduced accordingly, so that the curved states of the two curving portions can be easily adjusted.

Preferably, the driving portion is connected to a torque amount detector which is provided in the driving unit and which is configured to detect an amount of torque applied to the driving unit, the storage unit is configured to store the relation between torque and the curve amount of the second curving portion, the torque is applied to the driving unit and detected by the torque amount detector when the curve amount of the unloaded second curving portion is increased from an initial position, and the driving unit is configured to apply, to the driving unit, torque which is increased with the increase of the curve amount of the second curving portion and which is smaller than the torque corresponding to the curve amount of the second curving portion stored in the storage unit.

Thus, when the second curving portion is curved, the driving unit is driven by great torque in accordance with the curve amount of the second curving portion. Therefore, when external force is applied to the second curving portion, difference torque to maintain the curved state of the second curving portion is reduced, so that it is possible to more satisfactorily resist the external force.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
an insertion portion which includes a first bending portion and a second bending portion provided on the proximal side of the first bending portion, an initial position being set for the second bending portion;
an operation portion which is provided on the proximal side of the insertion portion, and which includes a first bending operation input portion configured to input a bending operation to bend the first bending portion;
an input amount detector which is configured to detect, as a bending operation input amount, the bending operation input to the first bending operation input portion;
a first bending drive mechanism which is configured to bend the first bending portion to a bending amount corresponding to the bending operation input amount;
a bending amount calculator which is configured to calculate a bending amount of the first bending portion driven to bend by the first bending drive mechanism;
a second bending drive mechanism which is configured to bend the second bending portion;
a driving portion which is coupled to the second curving drive mechanism and which is configured to generate driving force to drive the second bending drive mechanism;
a setting portion which is configured to set a first threshold and a second threshold, the first threshold being stored in advance and being compared with the bending amount of the first bending portion, the second threshold having an absolute value less than the absolute value of the first threshold and being compared with the first bending portion;
a determination portion which is configured to determine whether the bending amount of the first bending portion calculated by the bending amount calculator is more than the first threshold, and which is configured to determine whether the bending amount of the first bending portion calculated by the bending amount calculator is less than the second threshold; and
a controller which is configured to continuously output, to the driving portion, a bending drive signal that drives the second bending drive mechanism to bend the second bending portion in the same direction as the bending direction of the first bending portion when the determination portion determines that the bending amount of the first bending portion is more than the first threshold, and which is configured to output, to the driving portion, a bending drive signal that drives the second bending drive mechanism to return the second bending portion to the initial position when the determination portion determines that the bending amount of the first bending portion is less than the second threshold after the bending amount of the first bending portion has exceeded the absolute value of the first threshold.

2. The endoscope according to claim 1, wherein the driving portion is configured to generate torque to bend the second bending portion in accordance with the bending drive signal from the controller.

3. The endoscope according to claim 1, wherein
the second bending drive mechanism includes a wire which connects the driving portion and the second bending portion, and
the driving portion is configured to apply torque to the wire so that the controller prevents the second bending portion from bending in a direction opposite to the bending direction of the first bending portion.

4. The endoscope according to claim 1, wherein
the controller includes a storage portion,
the driving portion is connected to a torque amount detector which is provided in the driving portion and which is configured to detect an amount of torque applied to the driving portion,
the storage portion is configured to store the relation between torque and the bending amount of the second bending portion, the torque being applied to the driving portion and detected by the torque amount detector when the bending amount of the unloaded second bending portion is increased from the initial position, and
the driving portion is configured to apply, to the driving portion, torque which is increased with the increase of the bending amount of the second bending portion and which is smaller than the torque corresponding to the bending amount of the second bending portion stored in the storage portion.

5. The endoscope according to claim 1, wherein
the second bending drive mechanism includes a wire which connects the driving portion and the second bending portion, and
the driving portion is configured to apply tension to the wire to prevent the second bending portion from bending in a direction opposite to the bending direction of the first bending portion.

6. The endoscope according to claim 1, wherein
the second bending drive mechanism includes a wire which connects the driving portion and the second bending portion, and
the driving portion is configured to apply tension to the wire to return the second bending portion to the initial position when the input amount of the input amount detector is reduced to less than the absolute value of the second threshold which is less than the absolute value of the first threshold after the input amount of the input amount detector has exceeded the absolute value of the first threshold.

7. The endoscope according to claim 1, wherein
the controller includes a storage portion,
the second bending drive mechanism further includes a wire which couples the second bending portion and the driving portion, and a tension detector which is configured to detect tension applied to the wire,
the storage portion is configured to store the relation between tension and the bending amount of the second bending portion, the tension being applied to the wire via the driving portion and detected by the tension detector when the bending amount of the unloaded second bending portion is increased from the initial position, and
the driving portion is configured to apply, to the wire, tension which is increased with the increase of the bending amount of the second bending portion and which is smaller than the tension corresponding to the bending amount of the second bending portion stored in the storage portion.

8. The endoscope according to claim 1, wherein the absolute value of the first threshold is 90 degrees.

* * * * *